(12) United States Patent
Burns

(10) Patent No.: US 6,872,852 B2
(45) Date of Patent: Mar. 29, 2005

(54) POLYAMINE ANALOGUES AS CYTOTOXIC AGENTS

(75) Inventor: Mark R. Burns, Shoreline, WA (US)

(73) Assignee: MediQuest Therapeutics, Inc., Bothell, WA (US)

(*) Notice: Subject to any disclaimer, the term of this patent is extended or adjusted under 35 U.S.C. 154(b) by 0 days.

(21) Appl. No.: 10/239,521

(22) PCT Filed: Mar. 23, 2001

(86) PCT No.: PCT/US01/40360
§ 371 (c)(1),
(2), (4) Date: Sep. 23, 2002

(87) PCT Pub. No.: WO01/72685
PCT Pub. Date: Oct. 4, 2001

(65) Prior Publication Data
US 2003/0045755 A1 Mar. 6, 2003

Related U.S. Application Data
(60) Provisional application No. 60/191,839, filed on Mar. 24, 2000.

(51) Int. Cl.$^7$ ................. C07C 211/09; C07C 211/13; A61K 31/135
(52) U.S. Cl. ................. 564/306; 564/338; 564/367; 564/372; 514/649; 514/650
(58) Field of Search ................. 564/306, 338, 564/367, 372; 514/649, 650

(56) References Cited

U.S. PATENT DOCUMENTS

| | | | |
|---|---|---|---|
| 3,634,316 A | 1/1972 | Ito et al. | |
| 4,851,447 A | 7/1989 | Bey | |
| 5,677,350 A | 10/1997 | Frydman | |
| 5,886,185 A | 3/1999 | Chou et al. | |
| 5,962,533 A | 10/1999 | Bergeron, Jr. | |

FOREIGN PATENT DOCUMENTS

| | | |
|---|---|---|
| EP | A-0 162 413 | 11/1985 |
| EP | A-0 399 519 | 11/1990 |
| WO | WO 93 04373 | 4/1993 |
| WO | WO 94/19311 | 1/1994 |
| WO | WO 96 40096 A | 12/1996 |
| WO | WO 99 03823 | 1/1999 |

OTHER PUBLICATIONS

Database CAPLUS on STN, Acc. No. 1990:178908, Meisenheimer et al., Synthetic Communications (1989), 19(13–14), p. 2229–36 (abstract).*
Database CAPLUS on STN, Acc. No. 19978:748232, Lin et al., Chemistry (1997), 110(2), p. 131–139 (abstract).*
Database CAPLUS on STN, Acc. No. 1993:101619, Bruno et al., Anales de Quimica (1992), p. 267–9 (abstract).*
Database CAPLUS on STN, Acc. No. 1973:84220, Colautti et al., Bollettino Chimico Farmaceutico (1972), 111(10), p. 593–(abstract, RN=39779–60–7).*
Database CAPLUS on STN, Acc. No. 1973:84220, Colautti et al., Bollettino Chimico Farmaceutico (1972), 111(10), p. 593–(abstract, RN=39779–67–2).*
Database CAPLUS on STN, Acc. No. 1986:40682, Yan et al., Inorganica Chimica Acta (1985), 105(2), p. 121–8 (abstract).*
Database CAPLUS on STN, Acc. No. 1985:6101, Afsah et al., J. of the Chem. Soc., Perkin Transactions 1: Organic and Bio–organic chemistry (1972–1999) (1984), 8, p. 1929–32 (abstract).*
Database CAPLUS on STN, Acc. No. 1958:72438, Gassenmeier et al., DE 875523, May 4, 1953, abstract.*
Cancer Research, vol. 57, No. 2, 1997, pp. 234–239.
J. Med. Chem., vol. 41, No. 24, 1998, pp. 4723–4732.
J. Biol. Chem., vol. 268, No. 18, 1993, pp. 13151–13159.
Biological Chemistry Hoppe–Seyler, vol. 370, 1989, p. 525–531.
Chemical Abstracts, vol. 108, 1988, No. 221482j.
Chemical Abstracts, vol. 107, 1987, No. 89427t.
Chemical Abstracts, vol. 111, 1989, No. 33116f.
Chemical Abstracts, vol. 107, 1987, No. 146820s.
Judit Jakus, et al., Features of the Spermidine–binding Site of Deoxyhypusine Synthase as Derived from Inhibition Studies, The Journal of Biological Chemistry, vol. 268, No. 18, Issue of Jun. 25, pp. 13151–13159, 1993.
King, et al. The 2–Phenylpyrrolines: A redetermination of the Structures of the Supposed 2–Phenyl–$\Delta^3$–and $\Delta^4$ –pyrrolines., J. Chem. Soc. 1951, pp. 239–243.
Biochemical Pharmacology, vol. 36, No. 11, pp 1849–1852, 1987, Great Britain, Cytotoxic and non–cytotoxic N–alkyl derivatives of putrescine: effect on polyamine uptake and growth of prostatic cancer cells in vitro.
Libby, et al., Structure–Function Correlations Of Polyamine Analog–Induced Increases In Spermidine/Spermine Acetyltransferase Activity, Biochemical Pharmacology, vol. 38, No. 9, pp 1435–1442, 1989.
M. W. Read, et al., Synthesis of N{[4–2–Amino–4(3H)–oxo–5,6,7,8–tetrahydro–(9H)–pyrimido[4,5,–b]–azepin–6–yl)methyl]benzoyl}–L–glutamic Acid and Two of its Confromationally–Restricted Analogs, Tetrahedron 55 (1999) pp. 373–392.
C. W. Porter, et al., Relative Abilities of Bis(ethyl) Derivatives of Putrescine, Spermidine, and Spermine to Regulate Polyamine Biosynthesis and Inhibit L1210 Leukemia Cell Growth, Cancer Research 47, 47, 2821–2825, Jun. 1987.
R.J. Bergeron, et al., Synthetic Polyamine Analogues as Antineoplastics, J. Med. Chem. 1988, 31, pp. 1183–1190.
J. S. Large, et al., β–Adrenergic blocking agents. 19. 1–Phenyl–2–[[(substituted–amido) alkyl] amino]ethanols, Pharm. Div., ICI Ltd., J. Med. Chem. (1980), 23 (2), 112–17 Joural, abstract.

(List continued on next page.)

*Primary Examiner*—Brian Davis
(74) *Attorney, Agent, or Firm*—Connolly, Bove, Lodge & Hutz, LLP

(57) ABSTRACT

Cytotoxic polyamine analogues are provided that are useful for treating diseases where it is desired to inhibit cell growth and/or proliferation, for example cancer and post-angioplasty injury.

13 Claims, 26 Drawing Sheets

OTHER PUBLICATIONS

Beilstein Record No. 8216240, "4-(N-2,4-dimethoxybenzyl)aminobutanal diethylacetal", Feb. 29, 2000.

Beilstein Record No. 3285622, "4-benzylamino-butyraldehyde diethylacetal", Feb. 15, 1990.

* cited by examiner

Scheme 1

Putrescine n = 2
1,3-diaminopropane n = 1
1,5-diaminopentane n = 3

Aromatic Aldehyde

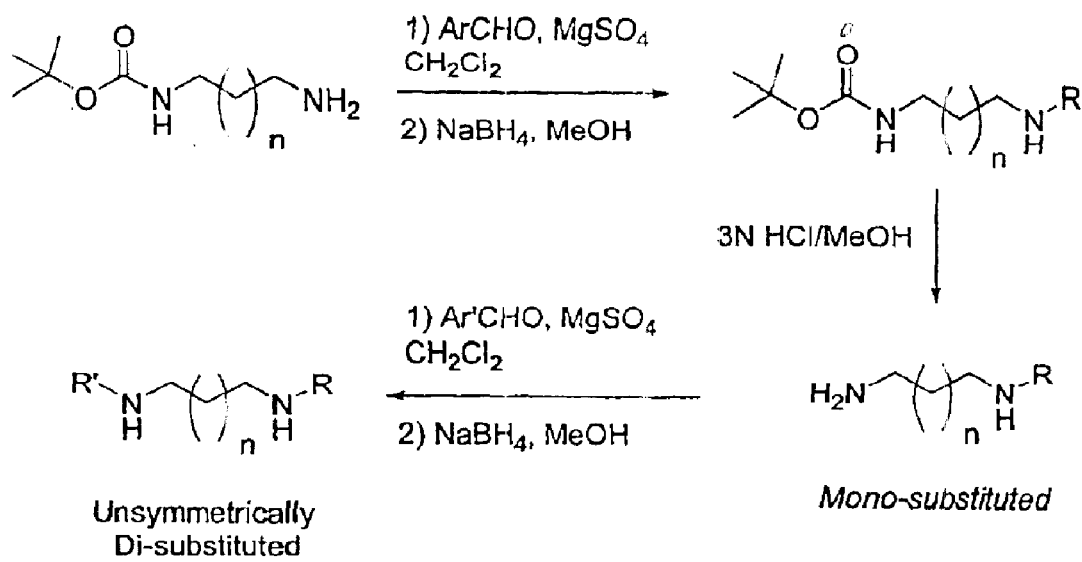
Figure 1B: Synthesis of mono- and unsymmetrically di-substituted analogs.

General Structure

| ANALOGUE | R GROUP | IC$_{50}$ MDA (μM) | IC$_{50}$ PC-3 (μM) |
|---|---|---|---|
| 1192 | (benzyl) | 192 | N.D. |
| 1191[b] | (pyridylmethyl) | 29 | N.D. |
| 1327 | (4-(diphenylamino)benzyl) | 0.38 | 0.4 |
| 1357 | (4-methoxy-1-naphthylmethyl) | 3 | 3.4 |
| 1361 | (4-benzyloxybenzyl) | 1.2 | 0.98 |
| 1362 | (2-naphthylmethyl) | 3.5 | 3.6 |
| 1356 | (9-anthracenylmethyl) | 5.5 | 3.6 |
| 1313 | (1-naphthylmethyl) | 10.8 | 13.2 |
| 1341 | (4-quinolinylmethyl) | 9.4 | 8.4 |
| 1307 | (3-nitrobenzyl) | 18.5 | 9.1 |

Figure 3

| | | | |
|---|---|---|---|
| 1312 | 4-ethylanisole | 21.4 | 5.9 |
| 1344 | 3-ethylbenzonitrile | 42.3 | 9.5 |
| 1353 | 5-ethyl-1,2,3-trimethoxybenzene | 58.5 | 58 |
| 1308 | 1-ethyl-2-nitrobenzene | 62.1 | 23 |
| 1358 | 5-ethyl-1,3-benzodioxole | 70.2 | 56 |
| 1343 | 3-ethyl-1H-indole | 77.1 | 51 |
| 1342 | 4-ethylbenzonitrile | 83.7 | 22 |
| 1332 | 4-ethyl-N,N-dimethylaniline | 197 | 56 |
| 1311 | 1-ethyl-4-nitrobenzene | 205 | 143 |
| 1326 | 3-ethylpyridine | >300 | 202 |
| 1325 | 2-ethylpyridine | >300 | >300 |
| 1314 | 4-ethylpyridine | 577 | 577 |
| 1497[b] | 4-ethylbiphenyl | 1.97 | 0.8 |

Figure 3

| | | | |
|---|---|---|---|
| 1493 | HN=N=N-C6H4-Et | 19.2 | 15.5 |
| 1474 | CHPh2-Et | 80.3 | 78.2 |
| 1473 | fluorenyl-Et | 12.1 | 1.95 |
| 1452 | 2-ethylthiophene | 201 | 192 |
| 1448 | 3-ethylthiophene | >50 | >50 |
| 1447 | 2-ethylthiazole | >300 | >300 |
| 1446 | 3,4-dichloro-ethylbenzene | 65.3 | 20.2 |

[b]Derived from 1,3-diaminopropane (n = 1)

| ID | Structure | Cell Line | IC50 (μM) |
|---|---|---|---|
| 1099 | 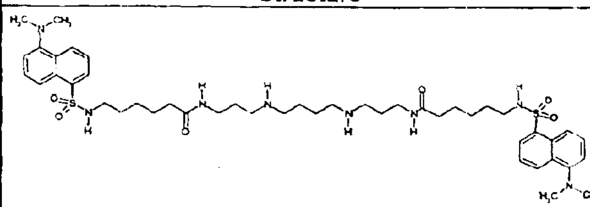 | MDA-MB-231 | 64 |
| 1132 | 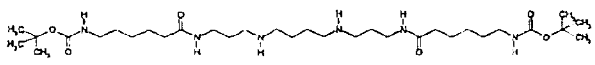 | | |
| 1133 | 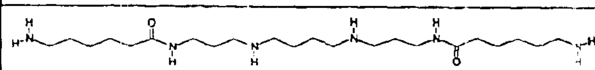 | | |
| 1168 | 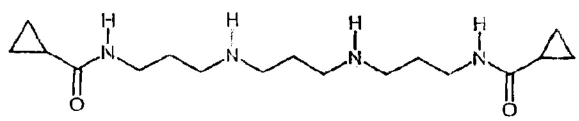 | MDA-MB-231 | >100 |
| | | NCI-H157 | >100 |
| 1242 | 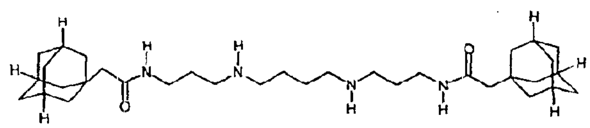 | MDA-MB-231 | 45.8 |
| | | PC-3 | 20.5 |
| 1250 | 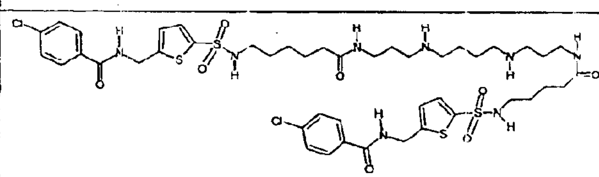 | | |
| 1258 | 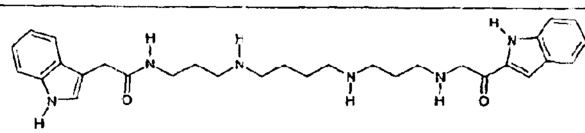 | MDA-MB-231 | >100 |
| 1266 | 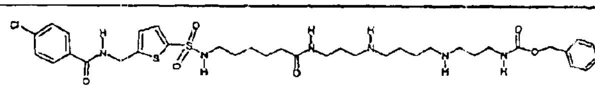 | MDA-MB-231 | 95.2 |
| 1270 | 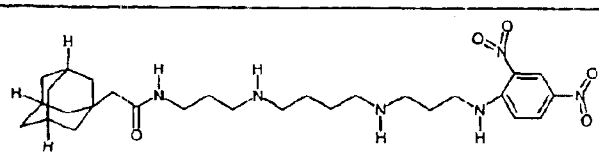 | MDA-MB-231 | 161 |
| | | PC-3 | 104 |
| 1276 | 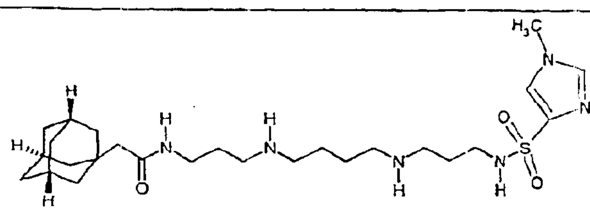 | MDA-MB-231 | >1.0 |

Figure 4

| # | Structure | Cell Line | Value |
|---|---|---|---|
| 1278 | (structure) | MDA-MB-231 | 19.6 |
| 1280 | (structure) | MDA-MB-231 | >100 |
| 1282 | (structure) | MDA-MB-231 | 59.2 |
|  |  | PC-3 | 120 |
| 1293 | (structure) | MDA-MB-231 | 2.0 |
|  |  | PC-3 | 1.9 |
|  |  | MDA-MB-231 | 2.03 |
|  |  | PC-3 | 1.81 |
|  |  | MDA-MB-231 | 0.60 |
|  |  | PC-3 | 0.51 |
| 1300 | (structure) | MDA-MB-231 | >300 |
| 1306 | (structure) | MDA-MB-231 | 198.0 |
|  |  | PC-3 | 42.83 |
| 1321 | (structure) | MDA-MB-231 | 55.9 |
|  |  | PC-3 | 25.6 |
| 1322 | (structure) | MDA-MB-231 | 9.4 |
|  |  | PC-3 | 15.2 |
| 1323 | (structure) | MDA-MB-231 | >300 |
|  |  | PC-3 | 147 |
| 1328 | (structure) |  |  |
| 1329 | (structure) |  |  |

Figure 4

| 1331 | [structure] | MDA-MB-231 | >300 |
| --- | --- | --- | --- |
| | | PC-3 | >300 |
| 1333 | [structure] | MDA-MB-231 | 156.7 |
| | | PC-3 | 83.6 |
| 1335 | [structure] | MDA-MB-231 | 195.5 |
| | | PC-3 | 60.9 |
| 1336 | [structure] | MDA-MB-231 | 195.2 |
| | | PC-3 | 199.5 |
| 1337 | [structure] | MDA-MB-231 | 64.1 |
| | | PC-3 | 24.9 |
| 1338 | [structure] | MDA-MB-231 | 6.4 |
| | | PC-3 | 6.4 |
| 1339 | [structure] | MDA-MB-231 | 185.5 |
| | | PC-3 | 183.5 |
| 1349 | [structure] | | |

Figure 11

| ID | Structure | Cell Line | IC50 (μM) |
|---|---|---|---|
| 1497 | 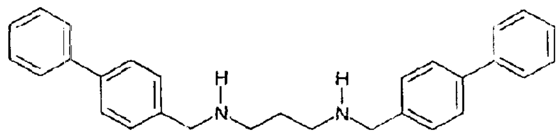 | PC-3 | 0.798 |
| | | SK-OV-3 | 0.816 |
| | | MDA-MB-231 | 1.97 |
| | | A375 | 0.666 |
| 1496 | 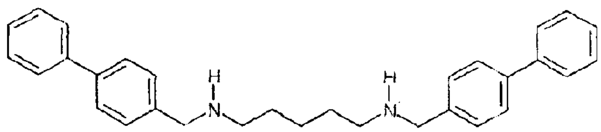 | PC-3 | 0.483 |
| | | SK-OV-3 | 0.514 |
| | | MDA-MB-231 | 1.31 |
| | | A375 | 0.53 |
| | | A375 | 0.59 |
| | | A375 | 0.67 |
| 1495 | 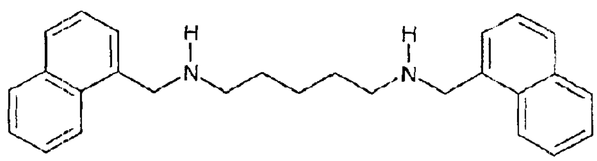 | PC-3 | 6.5 |
| | | SK-OV-3 | 6.86 |
| | | MDA-MB-231 | 8.31 |
| | | A375 | 5.75 |
| 1493 | 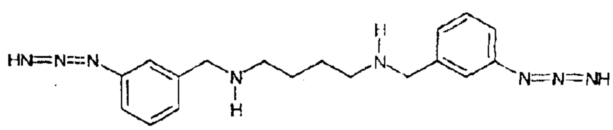 | PC-3 | 15.5 |
| | | SK-OV-3 | 17.7 |
| | | MDA-MB-231 | 19.2 |
| 1492 | 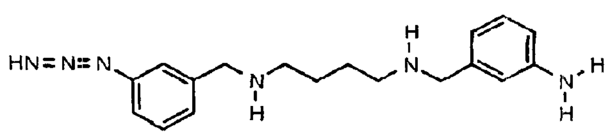 | PC-3 | 40.7 |
| | | SK-OV-3 | 74.5 |
| | | MDA-MB-231 | 98.3 |
| 1474 | 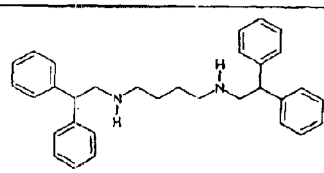 | PC-3 | 78.2 |
| | | SK-OV-3 | 203 |
| | | MDA-MB-231 | 80.3 |
| | | A375 | 73 |

Figure 11

| 1473 | [structure: bis-fluorenylmethyl diaminobutane] | PC-3 | 1.95 |
| --- | --- | --- | --- |
| | | SK-OV-3 | 1.89 |
| | | MDA-MB-231 | 12.1 |
| | | A375 | 0.908 |
| | | SK-Mel-28 | 0.664 |
| | | PC-3 | 1.73 |
| | | SK-OV-3 | 1.96 |
| | | MDA-MB-231 | 2.87 |
| | | A375 | 1.38 |
| | | PC-3 | 1.87 |
| | | MDA-MB-231 | 4.7 |
| | | A375 | 0.784 |
| 1452 | [structure: bis-(2-thienylmethyl) diaminobutane] | PC-3 | 192 |
| | | SK-OV-3 | 181 |
| | | MDA-MB-231 | 201 |
| | | A375 | 83.5 |
| 1451 | [structure: bis-(naphthylethyl) diaminobutane] | PC-3 | 36.9 |
| | | SK-OV-3 | 55.9 |
| | | MDA-MB-231 | 24.9 |
| | | A375 | 18.8 |
| 1448 | [structure: bis-(3-thienylmethyl) diaminobutane] | PC-3 | >50 |
| | | SK-OV-3 | >50 |
| | | MDA-MB-231 | >50 |
| | | A375 | 48 |
| | | MDA-MB-231 | |
| 1447 | [structure: bis-(2-thiazolylmethyl) diaminobutane] | PC-3 | >300 |
| | | MDA-MB-231 | >300 |
| | | A375 | >300 |
| | | SK-OV-3 | >300 |
| 1446 | [structure: bis-(3,4-dichlorobenzyl) diaminobutane] | PC-3 | 20.2 |
| | | MDA-MB-231 | 65.3 |
| | | A375 | 19.7 |
| | | SK-OV-3 | 41.7 |

| 1445 |  | MDA-MB-231 | 1.88 |
| --- | --- | --- | --- |
| | | PC-3 | 0.71 |
| 1441 |  | SK-Mel-28 | 2.16 |
| | | PC-3 | 16.3 |
| | | MDA-MB-231 | 7.62 |
| 1436 |  | PC-3 | 19.8 |
| | | MDA-MB-231 | 18.8 |
| | | A375 | 17.9 |
| | | SK-OV-3 | 20.5 |
| 1429 |  | MDA-MB-231 | 5 |
| | | PC-3 | 7 |
| | | SK-Mel-5 | 2 |
| | | A375 | 2 |
| 1427 |  | SK-Mel-5 | >15 |
| | | Mes-SA | >15 |
| | | Mes-SA/Dx5 | >15 |
| | | MDA-MB-231 | >15 |
| 1378 |  | PC-3 | 1100 |
| | | MDA-MB-231 | 600 |
| | | SK-Mel-5 | 150 |
| 1377 |  | PC-3 | 870 |
| | | MDA-MB-231 | 550 |
| | | SK-Mel-5 | 120 |

Figure 11

| 1376 | [structure] | MDA-MB-231 | >300 |
| --- | --- | --- | --- |
| | | PC-3 | >300 |
| 1375 | [structure] | MDA-MB-231 | 146 |
| | | PC-3 | 98 |
| 1374 | [structure] | MDA-MB-231 | >300 |
| | | PC-3 | >300 |
| 1370 | [structure] | MDA-MB-231 | >300 |
| | | PC-3 | >300 |
| 1368 | [structure] | MDA-MB-231 | 131.6 |
| | | PC-3 | 204.9 |
| 1367 | [structure] | MDA-MB-231 | 24.7 |
| | | PC-3 | 26.6 |
| 1366 | [structure] | MDA-MB-231 | >300 |
| | | PC-3 | >300 |
| 1365 | [structure] | MDA-MB-231 | >300 |
| | | PC-3 | >300 |
| 1364 | [structure] | MDA-MB-231 | 272 |
| | | PC-3 | 228 |

| 1363 |  | MDA-MB-231 | 15.8 |
| --- | --- | --- | --- |
| | | PC-3 | 14 |
| 1362 |  | MDA-MB-231 | 2.1 |
| | | PC-3 | 2.5 |
| | | MDA-MB-231 | 3.5 |
| | | PC-3 | 3.6 |
| 1361 |  | MDA-MB-231 | 2.1 |
| | | PC-3 | 2.2 |
| | | MDA-MB-231 | 1.2 |
| | | PC-3 | 0.98 |
| 1360 |  | MDA-MB-231 | 89.1 |
| | | PC-3 | 169.1 |
| 1359 |  | MDA-MB-231 | 295.3 |
| | | PC-3 | 349.1 |
| 1358 |  | MDA-MB-231 | 70.2 |
| | | PC-3 | 55.6 |
| 1357 |  | MDA-MB-231 | 2 |
| | | PC-3 | 2.1 |
| | | MDA-MB-231 | 3 |
| | | PC-3 | 3.4 |
| 1356 |  | MDA-MB-231 | 5.5 |
| | | PC-3 | 3.6 |

Figure 11

| | | | |
|---|---|---|---|
| 1353 | (structure: 3,4,5-trimethoxybenzyl-NH-(CH₂)₄-NH-CH₂-3,4,5-trimethoxyphenyl) | MDA-MB-231 | 58.5 |
| | | PC-3 | 58 |
| 1352 | (structure: 4-(diphenylamino)benzyl-NH-(CH₂)₂-NH-(CH₂)₃-NH-(CH₂)₂-NH-CH₂-4-(diphenylamino)phenyl) | MDA-MB-231 | 2 |
| | | PC-3 | 1.9 |
| 1346 | (structure: imidazoline-CH₂CH₂-N-piperidinyl-piperidinyl-N-CH₂CH₂-imidazoline) | PC-3 | 1100 |
| | | PC-3 | 1600 |
| | | MDA-MB-231 | 2100 |
| | | SK-Mel-5 | 720 |
| 1344 | (structure: 3-cyanobenzyl-NH-(CH₂)₄-NH-CH₂-3-cyanophenyl) | MDA-MB-231 | 42.3 |
| | | PC-3 | 9.5 |
| 1343 | (structure: indol-3-ylmethyl-NH-(CH₂)₄-NH-CH₂-indol-3-yl) | MDA-MB-231 | 77.1 |
| | | PC-3 | 51.4 |
| 1342 | (structure: 4-cyanobenzyl-NH-(CH₂)₄-NH-CH₂-4-cyanophenyl) | MDA-MB-231 | 83.7 |
| | | PC-3 | 22.2 |
| 1341 | (structure: quinolin-4-ylmethyl-NH-(CH₂)₄-NH-CH₂-quinolin-4-yl) | MDA-MB-231 | 9.4 |
| | | PC-3 | 8.4 |
| | | MDA-MB-231 | 21.8 |
| | | PC-3 | 15.7 |
| 1339 | (structure: PhCH(Ph)C(O)NH-(CH₂)₃-NH-(CH₂)₄-NH-(CH₂)₃-NHC(O)CH(Ph)Ph) | MDA-MB-231 | 185.5 |
| | | PC-3 | 183.5 |

Figure 11

| 1338 | [structure] | MDA-MB-231 | 6.4 |
| --- | --- | --- | --- |
| | | PC-3 | 6.4 |
| 1337 | [structure] | MDA-MB-231 | 64.1 |
| | | PC-3 | 24.9 |
| 1336 | [structure] | MDA-MB-231 | 195.2 |
| | | PC-3 | 199.5 |
| 1335 | [structure] | MDA-MB-231 | 195.5 |
| | | PC-3 | 60.9 |
| 1333 | [structure] | MDA-MB-231 | 156.7 |
| | | PC-3 | 83.6 |
| 1332 | [structure] | MDA-MB-231 | 197 |
| | | PC-3 | 56 |
| 1329 | [structure] | | |
| 1328 | [structure] | | |
| 1327 | [structure] | MDA-MB-231 | 0.6 |
| | | PC-3 | 0.7 |
| | | NCI-H157 | 0.56 |
| | | T-47D | 0.65 |
| | | SK-Mel-5 | 0.8 |
| | | Mes-SA | 0.64 |
| | | Mes-SA/Dx5 | 0.61 |
| | | A375 | 0.4 |
| | | MDA-MB-231 | 0.38 |
| | | PC-3 | 0.4 |

| 1326 |  | MDA-MB-231 | >300 |
| --- | --- | --- | --- |
| | | PC-3 | 202 |
| 1325 |  | MDA-MB-231 | >300 |
| | | PC-3 | >300 |
| 1322 |  | MDA-MB-231 | 9.4 |
| | | PC-3 | 15.2 |
| 1321 |  | MDA-MB-231 | 55.9 |
| | | PC-3 | 25.6 |
| 1318 |  | MDA-MB-231 | 192 |
| | | PC-3 | 49.8 |
| 1317 |  | MDA-MB-231 | 158.1 |
| | | PC-3 | 66 |
| 1316 |  | MDA-MB-231 | >1 mM |
| | | PC-3 | >1 mM |
| 1314 |  | MDA-MB-231 | 576.8 |
| | | PC-3 | 166.4 |
| 1313 |  | MDA-MB-231 | 6.4 |
| | | NCI-H157 | 8.1 |
| | | PC-3 | 8.2 |
| | | T-47D | 6.5 |
| | | SK-Mel-5 | 3.4 |
| | | Mes-SA | 10 |
| | | Mes-SA/Dx5 | 7.2 |
| | | A375 | 4.8 |
| | | MDA-MB-231 | 10.8 |
| | | PC-3 | 13.2 |
| 1312 |  | MDA-MB-231 | 21.4 |
| | | PC-3 | 5.9 |

Figure 11

| 1311 | [structure: HO-N(=O)-C6H4-CH2-NH-(CH2)4-NH-CH2-C6H4-N(=O)-OH] | MDA-MB-231 | 135.2 |
| --- | --- | --- | --- |
| | | MDA-MB-231 | 275 |
| | | PC-3 | 41.8 |
| | | PC-3 | 244 |
| 1310 | [structure] | MDA-MB-231 | >1000 |
| 1308 | [structure: 2-NO2-C6H4-CH2-NH-(CH2)4-NH-CH2-C6H4-2-NO2] | MDA-MB-231 | 62.1 |
| | | PC-3 | 23.2 |
| 1307 | [structure: 3-NO2-C6H4-CH2-NH-(CH2)4-NH-CH2-C6H4-3-NO2] | MDA-MB-231 | 18.5 |
| | | PC-3 | 9.1 |
| | | NCI-H157 | 6.9 |
| 1306 | [structure: thiophene-CH2-C(=O)-NH-(CH2)3-NH-(CH2)3-NH-(CH2)3-NH-C(=O)-CH2-thiophene] | MDA-MB-231 | 198 |
| | | PC-3 | 42.83 |
| 1303 | [structure: H2N-(CH2)4-NH-CH2-naphthyl] | MDA-MB-231 | 23.2 |
| | | PC-3 | 7.7 |
| | | NCI-H157 | 11.8 |
| 1302 | [structure: H2N-(CH2)4-NH-CH2-C6H4-N(=O)-OH] | MDA-MB-231 | 201 |
| | | PC-3 | 50.4 |
| 1301 | [structure: H2N-(CH2)4-NH-CH2-C6H5] | MDA-MB-231 | >300 |
| | | PC-3 | 211 |

Figure 11

| 1293 | [structure] | MDA-MB-231 | 2 |
| --- | --- | --- | --- |
| | | PC-3 | 1.9 |
| | | MDA-MB-231 | 2.03 |
| | | PC-3 | 1.81 |
| | | MDA-MB-231 | 0.6 |
| | | PC-3 | 0.51 |
| | | NCI-H157 | 5.3 |
| 1282 | [structure] | MDA-MB-231 | 59.2 |
| | | PC-3 | 120 |
| 1192 | [structure] | MDA-MB-231 | 192 |
| 1191 | [structure] | MDA-MB-231 | 28.8 |

POLYAMINE ANALOGUES AS CYTOTOXIC AGENTS

RELATED APPLICATIONS

This application is related to U.S. patent application Ser. No. 09/396,523, filed Oct. 15, 1999, which is hereby incorporated by reference as if fully set forth.

FIELD OF THE INVENTION

The invention in the field of chemistry and biochemistry relates to the synthesis and use of novel polyamine analogue compounds with pharmacological or agricultural uses as cytotoxic agents. As drugs, these compounds are used to treat disorders of undesired cell proliferation, primarily cancer, alone or combined with other cytotoxic or antiproliferative agents.

BACKGROUND OF THE INVENTION

Decades of research on the myriad of biological activities that the polyamines, putrescine, spermidine and spermine play in cellular processes have shown the profound role they play in life (Cohen, S. S., "A Guide to the Polyamines" 1998, Oxford University Press, New York). As polycations at physiological pH, they bind tightly to and strongly modulate the biological activities of all of the anionic cellular components. Specific and strong interactions have been associated with DNA and RNA together with their associated chromatin proteins (Tabor, H. et al. 1,4-Diaminobutane (putrescine), spermidine, and spermine. *Ann Rev. Biochem.* 1976, 45, 285–306; Matthews, H. R. Polyamines, chromatin structure and transcription. *BioEssays*, 1993, 15, 561–566). Specific interactions of multicationic polyamines with microtubules has been recently shown (Wolff, J. Promotion of Microtubule Assembly by Oligocations: Cooperativity between Charged Groups. *Biochemistry*, 1998, 37, 10722–10729; Webb, H. K. et al., 1-(N-Allylamino)-11-(N-ethylamino)-4,8-diazaundecanes alter tubulin polymerization. *J Med. Chem.* 1999 42(8):1415–21). Allosteric regulation of membrane-bound enzymes including acetylcholinesterase has been shown (Kossorotow, A. et al. Regulatory effects of polyamines on membrane-bound acetylcholinesterase. *Biochem. J.* 1974, 144, 21–27).

There have also been reports on the involvement of polyamines in the induction of apoptosis. Stefanelli and coworkers report that using HL60 human leukemia cells (Stefanelli, C. et al. Spermine causes caspase activation in leukaemia cells. *FEBS Letters*, 1998, 437, 233–236) or a cell-free model (Stefanelli, C. et al. Spermine triggers the activation of caspase-3 in a cell-free model of apoptosis. *FEBS Letters*, 1999, 451, 95–98), addition of spermine led to the induction of apoptosis. This process was characterized by the release of cytochrome c from mitochondria, the dATP-dependent processing of pro-caspase-3 and the onset of caspase activity. This caspase activation was not blocked by antioxidants or inhibition of polyamine oxidase by MDL 72527. Thus these workers hypothesize a physiological role for the polyamines in the transduction of a death message.

Due to its four positive charges at physiological pH, spermine is predominantly bound to cellular components and its free concentration in the cell is very low despite the high cellular content of this polyamine (Marton, L. J. et al. Polyamines as targets for therapeutic intervention. *Annu. Rev. Pharmacol. Toxicol.* 1995, 35, 55–91). Thus, spermine may have the characteristics of a damage-sensing molecule, since its free concentration may increase rapidly following insults to nucleic acids, membranes or other storage sites. This increase would be proportional to the extent of the damage and could transduce a death signal to the mitochondria.

Other workers have explored the toxic mechanisms of polyamines and polyamine analogs. Poulin and coworkers showed that the deregulation of polyamine transport in L1210 cells over-expressing ornithine decarboxylase (ODC) led to a lethal accumulation of spermidine (Poulin, R. et al. Induction of apoptosis by excessive polyamine accumulation in ornithine decarboxylase-overproducing L1210 cells. *Biochem. J* 1995, 311, 723–727). They showed that this lethal insult was due to the induction of apoptosis. Polyamine oxidation was not responsible for the apoptosis observed. Wallace and coworkers showed a similar non-oxidative lethal action of spermine in BHK-21/C13 cells (Brunton, V. G. et al. Mechanisms of spermine toxicity in baby-hamster kidney (BHK) cells. *Biochem. J.* 1991, 280, 193–198). They also showed that MDL 72527 exacerbated the toxic effects of spermine.

Packham and Cleveland showed that the forced expression of ODC in 32D.3 murine myeloid cells caused an apoptotic cell death following IL-3 withdrawal (Packhani, G. et al. Ornithine decarboxylase is a mediator of c-myc-induced apoptosis. *Mol. Cell. Biol.* 1994, 14, 5741–5747). ODC induced cell death in a dose-dependent fashion, and α-difluoromethylornithine (DFMO), an irreversible inhibitor of ODC effectively blocked ODC-induced cell death. Gerner and coworkers, in a series of experiments with ODC over-expressing or polyamine transport regulation deficient cell lines, demonstrated that loss of feedback regulation on the polyamine transport system is sufficient to induce apoptosis (Xie, X. et al. Loss of intracellular putrescine pool-size regulation induces apoptosis. *Exp. Cell Res.* 1997, 230, 386–392). Loss of regulation of the tight feedback controls on putrescine levels caused the cells to undergo apoptosis in a putrescine dose-dependant manner.

Yanagawa and coworkers showed that the antiproliferative effects of hepatocyte growth factor (HGF) involved the induction of apoptosis via an increase in ODC activity with a resultant increase in intracellular polyamine levels (Yanagawa, K. et al. The antiproliferative effect of HGF on hepatoma cells involves induction of apoptosis with increase in intracellular polyamine concentration levels. *Oncol. Rep.* 1998, 5, 185–190). Addition of the ODC inhibitor DFMO reduced the levels of polyamines and inhibited the apoptotic effects of HGF. This inhibition of apoptotic effects was again reversed by the addition of exogenous polyamines to the cells. The above reports indicate a clear apoptotic effect upon loss of regulation of polyamine pool concentrations. It is also clear that these effects occurred through a non-oxidative mechanism.

A series of modified spermine analogs, typified by $N^1$, $N^{11}$-diethylnorspermine (BE-3,3,3 also known as DENSPM), have been shown to super-induce the polyamine catabolic enzyme spermidine/spermine $N^1$-acetyltransferase (SSAT) and to work partially through an oxidative mechanism (Casero, R. A. et al. Spermidine/spermine $N^1$-acetyltransferase—the turning point in polyamine metabolism. *FASEB J.* 1993, 7, 653–661). Porter and coworkers explored the cellular responses to a series of these analogs and compared their cytotoxicity, induction of SSAT and effects on the cell cycle (Kramer, D. L. et al. Effects of novel spermine analogues on cell cycle progression and apoptosis in MALME-3M human melanoma cells. *Cancer Res.* 1997, 57, 5521–5527). They concluded that cytotoxicity could not be correlated with the level of SSAT induction by these analogs, which left open the possibility that additional mechanism(s) could be involved. With only small changes in the analog's structure, great variability was seen in the effects on the cell cycle.

Using related analogs, Hu and Pegg showed that the deregulated uptake of polyamine analogs by the polyamine transporter caused rapid induction of apoptosis (Hu, R-H. et al. Rapid induction of apoptosis by deregulated uptake of polyamine analogues. *Biochem. J.* 1997, 328, 307–316).

Certain dibenzylputrescine analogs have been shown to have anti-proliferative effects against human and rodent tumor cell lines. Frydman et al. describe the cytotoxicity against three squamous cell carcinoma lines (SCC-38, SCC-4Y and SCC-13Y) and a rat hepatoma cell line (H-4-II-E) of the $N^1$, $N_4$-dibenzyl analogs of 1,3-diaminopropane, putrescine and cadaverine (Aizencang, G. et al. Antiproliferative effects of $N^1$, $N^4$-dibenzylputrescine in human and rodent tumor cells. *Cellular and Molecular Biology,* 1998, 44 (4), 615–625 and U.S. Pat. No. 5,677,350). $IC_{50}$ values of between 100 to 300 μM were found against these cell lines with the putrescine and cadaverine $N^1$, $N^4$-dibenzyl analogs. These researchers describe the classic hallmarks of cells undergoing apoptotic cell death: vacuole formation, decrease in size, changes in staining by trypan blue and adherence.

Frydman et al. also demonstrated that co-incubation with a specific polyamine oxidase inhibitor, $N^1$, $N^4$-bis(buta-2,3-dienyl)butanediamine (MDL 72527) caused a five-fold increase in the activity of the analogs. Although a moderate inhibition of [1,4-$^{14}$C]-putrescine uptake was found ($K_{iapp}$=6.5+/−1.7 μM with $N^1$, $N^4$-dibenzylputrescine compared to $K_{mapp}$=5.2+/−0.6 μM for putrescine), even a ten-fold excess of putrescine over $N^1$, $N^4$-dibenzylputrescine could not abolish its cell growth inhibitory effect. Moderate reductions in levels of intracellular polyamines were measured after 72 h of drug treatment. These decreases in the polyamine levels are of minor significance in comparison to the decreases achieved with therapeutic approaches designed to deplete polyamines (see U.S. Pat. No. 6,172,261 B1).

Results from an in vivo antiproliferative study using $N^1$, $N^4$-dibenzylputrescine (U.S. Pat. No. 5,677,350), suggested great promise for these analogs. These studies showed significant reduction in the weights of the treated compared to control tumors. Nude mice aged four weeks were subcutaneously inoculated with rat hepatoma H-4-II-E cells (10× $10^6$ cells) or human melanoma II-B-Mel-J (5×$10^6$ cells) and allowed to develop for 15 to 24 days. Administration of 0.15% $N^1$, $N^4$-dibenzylputrescine in the drinking water over 10 weeks showed no toxic effects on the animals. Several key observations were made in conjunction with these experiments. As stated above, the treatment with $N^1$, $N^4$-dibenzylputrescine showed no liver or kidney damage following the treatment. Metastatic lung tumors that were observed in the control animals did not appear in the treated animals. Most importantly, the growth of the tumors was strongly inhibited by a factor of 6 or 7-fold in the treated animals. Further study showed no significant changes in the polyamine levels in the tumors from the treated in comparison to the control animals.

A recent report suggests an explanation for the increased cytotoxicity observed in the presence of MDL 72527 (Dai, H. et al. The polyamine oxidase inhibitor MDL-72,527 selectively induces apoptosis of transformed hematopoietic cells through lysosomotropic effects. *Cancer Research,* 1999, 59, 4944–4954). This compound, previously reported to be a relatively non-toxic, selective polyamine oxidase (PAO) inhibitor, was shown to induce apoptosis in transformed hematopoietic cells. It is interesting to note that this compound was non-toxic to primary myeloid progenitors. Cellular characterization of this compound revealed features strikingly similar to those reported for the dibenzylputrescine analogs above. Although this compound decreased the levels of putrescine and spermidine (it also increased the level of $N^1$-acetylspermidine), these effects were expected based on the compound's action as an inhibitor of PAO. The cytotoxic effects of this compound were not blocked by co-treatment with exogenous putrescine or spermidine. These effects were also not influenced by over-expression or inhibition of ornithine decarboxylase (ODC), the rate-limiting polyamine biosynthetic enzyme. A well-characterized specific inhibitor of ODC, DFMO caused the increased uptake of MDL 72527 leading to greater cytotoxicity but treatment with putrescine/DFMO/MDL 72527 gave the same effects as MDL 72527 alone.

In summary, these reports showed that $N^1$, $N^4$-dibenzylputrescine and other similar analogs were not cytotoxic by depleting the intracellular polyamine levels. The fact that a specific and potent PAO inhibitor increased their activity suggested that a polyamine oxidase-mediated mechanism was not responsible. Despite this limited knowledge about the mechanism, these compounds did show moderate $IC_{50}$ values against several different cancer cell lines. They also showed the hallmarks of compounds that operate through an apoptotic mechanism. $N^1$, $N^4$-dibenzylputrescine showed significant promise in a mouse xenograft anti-tumor model. This compound was orally active and showed no toxic effects even after a 40-day treatment. Additional advantages of these compounds have been their easy and inexpensive synthesis.

Mitochondria apparently play a major role in apoptotic pathways. It is now generally accepted that a decrease in the mitochondrial membrane potential is an early universal event of apoptosis (Mignotte, B. et al. Mitochondria and apoptosis. *Eur. J Biochem.* 1998, 252, 1–15). Mitochondria participate in the early steps of apoptosis, in response to many stimuli, through the release of cytochrome c into the cytoplasm. Recent literature reports indicate that many molecules, including several clinically promising agents, induce apoptosis through the release of cytochrome c from the mitochondria. One well-established mechanism for this release is the swelling of the mitochondrial inner membrane followed by rupture of the outer membrane/matrix. The release of the positively charged cytochrome c protein from the mitochondria is strongly linked to the induction of apoptosis (Green, D. R. et al. Mitochondria and Apoptosis. *Science,* 1998, 281, 1309–1312). The released cytochrome c initiates a complex pathway that ultimately results in the activation of caspase-3.

Tamanoi and coworkers showed that a set of four structurally diverse farnesyltransferase inhibitors induce the release of cytochrome c from mitochondria of v-K-ras-transformed normal rat kidney cells (Suzuki, N. et al. Farnesyltransferase inhibitors induce cytochrome c release and caspase 3 activation preferentially in transformed cells. *Proc. Natl. Acad. Sci. USA,* 1998, 95, 15356–115361). They showed that this release resulted in caspase-3 activation and was observed preferentially in transformed cells compared to the normal cells.

Debatin and coworkers showed that betulinic acid, a melanoma-specific cytotoxic agent, triggered CD95 (APO-1/Fas)- and p53-independent apoptosis via release of cytochrome c and apoptosis inducing factor (AIF) from the mitochondria into the cytosol (Fulda, S. et al. Activation of mitochondria and release of mitochondrial apoptogenic factors by betulinic acid. *J. Biol. Chem.* 1998, 273, 33942–33948). The fact that this drug-induced apoptosis (via a direct effect on mitochondria) did not involve two common resistance mechanisms suggests that betulinic acid may bypass some forms of drug resistance (Fulda, S. et al. Betulinic acid triggers CD95 (APO-1/Fas)- and p53-independent apoptosis via activation of caspases in neuroectodermal tumors. *Cancer Res.* 1997, 57, 4956–4964).

An additional agent, presently in Phase III trials of metastatic breast and ovarian cancer, lonidamine (1-[(2,4-dichlorophenyl)methyl]-1H-indazole-3-carboxylic acid), also acts independently of p53 status via a direct action on the mitochondrial permeability transition pore (Ravagnan, L. et al. Lonidamine triggers apoptosis via a direct, Bcl-2-inhibited effect on the mitochondrial permeability transition pore. *Oncogene* 1999, 18, 2537–2546).

The early universal apoptotic event of a decrease in the mitochondrial membrane potential may occur by the opening of pores in the inner membrane of mitochondria. These pores allow the passage of compounds of molecular weight of <1500 Da through the membrane and several of these have been directly linked to the induction of apoptosis.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention relates to the synthesis and growth inhibitory properties of polyamine analogues and their use as drugs, as agricultural or as environmentally useful agents. Preferably, the analogues are derivatives of spermine, spermidine and putrescine, such as derivatives of dibenzylputrescine.

The analogues of the present invention include derivatives of spermine, spermidine and putrescine, as well as analogs thereof, substituted at one or both of their terminal (alpha, or α, and omega, or ω) nitrogen atom positions. Preferred analogues are substituted at both positions. The substitutions may be with the same or different chemical moieties. Moreover, the analogues may be substituted at one or more internal nitrogen and/or carbon positions along the polyamine backbone by a low molecular weight chemical moiety.

A preferred embodiment is a highly cytotoxic analogue with pharmaceutical utility as an anti-cancer chemotherapeutic. Such an analogue would have an $IC_{50}$ in the micromolar or submicromolar range against tumor cells. Preferred compounds with such activity include compounds 1313 and 1327 as described herein. Additional preferred compounds include spermine analogues substituted at both terminal nitrogen atoms by identical substituents.

Preferred substituents are structures that increase cytotoxicity or otherwise enhance the inhibition of cell growth, proliferation, metastases, or neoplasm. Such additional substituents include the aziridine group and various other aliphatic, aromatic, mixed aliphatic-aromatic, or heterocyclic multi-ring structures.

More specifically, a polyamine analogue or derivative of the invention includes one that is cytotoxic and has the formula:

wherein
$R_1$ and $R_2$ are independently H or a moiety selected from the group consisting of a straight or branched $C_{1-10}$ aliphatic, alicyclic, single or multi-ring aromatic, single or multi-ring aryl substituted aliphatic, aliphatic-substituted single or multi-ring aromatic, a single or multi-ring heterocyclic, a single or multi-ring heterocyclic-substituted aliphatic and an aliphatic-substituted aromatic, and halogenated forms thereof; and X is a polyamine with two terminal amino groups, —(CH$_2$)$_3$—NH—, or —CH$_2$—Ph—CH$_2$—.

Preferably, the polyamine is linear or selected from spermine, spermidine, or putrescine. $R_1$ and $R_2$ may be identical or different and are preferably not simultaneously unsubstituted benzyl moieties. Halogenated moieties include those substituted with fluorine, chlorine, bromine, and iodine.

Alternatively, X is —(CH$_2$)$_3$—NH— or —CH$_2$—Ph—CH$_2$—, where "Ph" represents a phenyl moiety, and $R_1$ and $R_2$ are as described above.

Disubstituted polyamine analogues, preferably also containing a reporter group, may also be employed as assay or biochemical probes.

Once a cytotoxic polyamine analogue has been identified, it can readily be further optimized by structural and functional comparisons with other polyamine analogues to improve its utility. Examples of such improvements include, but are not limited to, increased cytotoxicity, enhanced metabolic stability, enhanced specificity, ease of handling and administration, non-incorporation into cellular polyamine pools, and decreases in side effects.

The present invention is also directed to compositions comprising a polyamine analog. Preferably, the composition is a pharmaceutical formulation useful for treating a disease or condition in which the inhibition of cell growth or proliferation is desirable, comprising a composition as described above and a pharmaceutically acceptable excipient. The pharmaceutical composition may further include additional cytotoxic compounds or an inhibitor of polyamine synthesis, such as DFMO. Other combinations include the above pharmaceutical composition and one or more additional agents otherwise known to be useful for treating said disease or condition This invention also provides a method for inhibiting cell growth or proliferation comprising contacting the cell(s) with an analogue of the invention. Such methods include treating a disease or a condition in a subject associated with undesired cell proliferation by administering to said subject an effective amount of a pharmaceutical composition as described above. The undesired cell proliferation may be associated with proliferation of cells of the immune system, cells of the vascular neontima, tumor cells or with undesired angiogenesis. Preferred diseases to be treated as above include cancer or post-angioplasty injury.

Thus the analogues of the invention, alone or in combination with other agents, may be used for the treatment of cancer and other diseases of unwanted cellular proliferation, including angiogenesis and post-injury cell growth. Preferably, such treatments act by inhibiting cell growth or by the induction of apoptosis. As such, they may act by cytostatic and/or cytotoxic mechanisms. The analogues of the invention, individually or in combinations with or without other agents, may also be used to treat hypertension, osteoporosis, Alzheimer's disease, ischemia, autoimmune diseases, psychosis, depression, strokes, cardiovascular disease, allergies, asthma, tissue rejection during transplantation, infection with microorganisms or parasites, as well as plant pathogens including fungi. The analogues of the invention may also be efficacious as anti-diarrheal, anti-peristaltic, anti-spasmodic, anti-viral, anti-psoratic and insecticidal agents.

The present invention is also directed to a series of polyamine analogues useful in diagnostic compositions. Methods for the synthesis of such compounds are also described.

DETAILED DESCRIPTION

Figure 1:
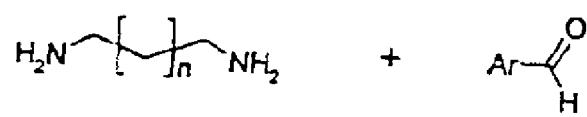
FIG. 1A shows a reaction scheme for the production of polyamine analogs within the scope of the invention.
FIG. 1B shows the synthesis of mono- and unsymmetrically disubstituted analogs.
Figure 1:
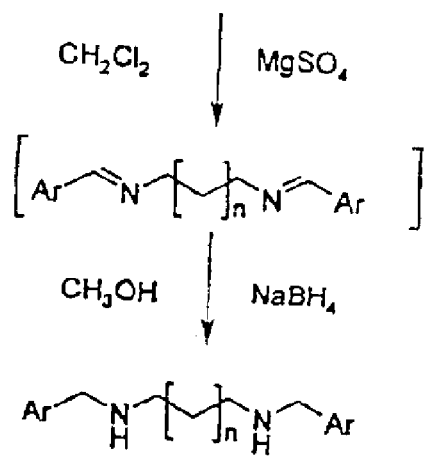

The present inventor has designed novel polyamine analogue compounds displaying both in vivo and in vitro cytotoxicity. Such compounds are useful as drugs in a number of diseases, particularly cancer. They can also be used as a component of novel drug combinations with, for example, a polyamine synthesis inhibitor such as DFMO (which inhibits ornithine decarboxylase) or with other cytotoxic agents. A compound of the present invention is generally useful in diseases or conditions in which inhibition of cell growth is desirable, and also has agricultural and environmental uses based on its cytotoxicity.

The inventor found that various chemical groups can be attached to a polyamine to give it advantageous properties as an inhibitor of cell growth and/or proliferation.

In a preferred aspect of the invention, the analogues are advantageous in the treatment of human melanoma. Human melanoma is a growing health problem in the United States and much of the world. Increased solar radiation exposure due to ozone depletion makes this disease a profound health concern for aging populations and for future generations. Malignant melanoma is considered to be a chemotherapy-refractory tumor and commonly used anticancer drugs do not appear to modify the prognosis of metastatic disease (Serrone, L. et al. The chemoresistance of human malignant melanoma: an update. Melanoma Res. 1999, 9, 51–58). Preferred embodiments of the polyamine analogues of the invention have been found to display dramatic selectivity toward melanoma cell lines.

Definitions

As used herein, the term "polyamine" includes naturally occurring polyamines, such as putrescine, spermine or spermidine, as well as other naturally occurring polyamines, such as caldopentamine, homocaldopentamine, $N^4$-bis (aminopropyl)norspermidine, thermopentamine, $N^4$-bis (aminopropyl)spermidine, caldohexamine, homothermohexamine and homocaldohexamine, cadaverine, aminopropylcadaverine, homospermidine, caldine (norspermidine), 7-hydroxyspermidine, thermine (norspermine), thermospermine, canavalmine, aminopropylhomospermidine, and aminopentylnorspermidine.

The term also embraces longer linear polyamines, branched polyamines, and the like, which may have between 2 and about 10 nitrogen atoms. The nitrogen atoms are generally separated by 2 to 6 carbon atoms along the linear chain. Also included in this definition are polyamine derivatives or analogues comprising a basic polyamine chain with any of a number of functional groups covalently bonded to a C atom or a terminal or internal N atom. These include $N^1$-monosubstituted polyamine analogues, as well as substitution of carbon atoms α to secondary nitrogens and acylation of nitrogens to slow degradation by polyamine oxidase. The selective primary mono-substitution of polyamines is known (Krapcho, A. P. et al. Mono-protected diamines. N-tert-butoxylcarbonyl-α,ω-alkanediamines from α,ω-alkanediamines. Syn. Comm. 1990, 20, 2559–2564; Blagbrough, I. S. et al. Practical Synthesis of unsymmetrical polyamine amides. Tetrahedron Lett. 1998, 39, 439–442). Alternatively, methyl groups can be introduced α to the terminal amino groups of spermine (Lakanen, J. R. et al., J. Med. Chem. 35:724–734, 1992).

Various polyamine analogues alkylated at internal carbons can also be readily synthesized. 5-carboxyspermine, tetra tBoc-5-carboxyspermine and its acid chloride are synthesized according to Huber, H. et al., J. Biol. Chem. 271:27556–27563, 1994. The resulting acid chloride can then be reacted with various nucleophilic reagents to produce carboxy-substituted polyamine analogues following removal of the tBoc group. Alternatively, the carboxy intermediate can be reduced to an intermediate that is used to synthesize numerous additional analogues.

A "reporter moiety" is a chemical moiety forming part of a probe which renders the probe detectable (either directly or, for example, through enzymatic enhancement) and hence permits the localization of the probe. A reporter is detectable either because it itself emits a detectable signal, or by virtue of its affinity for a reporter-specific partner which is detectable or becomes so by binding to, or otherwise reacting with, the reporter.

The various polyamine analogue compounds disclosed herein are identified by an identifier number scheme (using four digit compound numbers alone or in combination with an "ORI", or "Ori" identifier). Irrespective of what identifying scheme is used, the identifier merely represents the actual molecular structure of the compound involved and imposes no limitation on said compound.

Polyamine Analogue Structure and Synthesis

The polyamine analogues of the present invention are generally substituted or derivatized forms of existing or novel polyamines. Preferably, the analogues are derivatives of spermine, spermidine and putrescine. More preferably, the analogues are substituted at least at one or both of the terminal (alpha, or α, and omega, ω) nitrogen atom positions of an underlying polyamine. The analogues are preferably substituted at both positions. Most preferred are analogues with an $IC_{50}$ against tumor cells in the micromolar range (including from 1 to about 600, 1 to about 300, 1 to about 200, 1 to about 100, 1 to about 50, 1 to about 20, 1 to about 15, 1 to about 10, 1 to about 9, 1 to about 8, 1 to about 7, 1 to about 6, 1 to about 5, 1 to about 4, 1 to about 3, and 1 to about 2 $\mu$M) and submicromolar range (including from about 0.01 to 1, about 0.1 to 1, about 0.2 to 1, about 0.3 to 1, about 0.4 to 1, about 0.5 to 1, about 0.6 to 1, about 0.7 to 1, about 0.8 to 1, and about 0.9 to 1 $\mu$M).

FIG. 1A shows an exemplary reaction Scheme I for the production of substituted polyamines that have 3, 4 or 5 carbon atoms separating two terminal amino groups in a linear chain. This reaction is an extremely direct synthetic method and may be conducted in a single reaction vessel. The exemplary polyamine reactant with 4 carbon atoms is putrescine. The product of the reaction using putrescine is $N^1,N^4$-dibenzylputrescine. Following the reaction, the polyamine analogues are readily purified by column chromatography or crystallization.

Similar reactions can be conducted with spermine, spermidine and other polyamines to produce analogues of the invention. Such additional reactions are known in the art and may include appropriate steps to protect functional groups within the structures of larger polyamines such as spermine and spermidine.

The reaction scheme in FIG. 1A is readily modified to produce cytotoxic polyamine analogues of the invention by the use of aldehydes other than the exemplary aromatic aldehyde indicated. Thus reactions with aldehydes containing cyclic or aliphatic moieties, as well as substituted forms thereof may be used to produce additional analogues of the invention. Cyclic moieties may of course be either homocyclic or heterocyclic, as well as aromatic or aryl, to permit production of the analogues of the invention. The aliphatic moieties may of course contain one or more non-carbon heteroatoms.

Examples of cyclic moieties include multi-ring and multi-single-ring groups as well as the bonds or straight chain groups that attach different ring structures in a multiple ring head group. Examples of such groups for covalent attachment of a ring structure are amide, sulfonamide, ether, thioether, ester, —C—C— and —C—N— and —N—N— bonds. The ring structures can also be individually substituted.

Examples of heterocyclic moieties include, but are not limited to, pyrrolidinyl, piperidinyl, piperazinyl, morpholinyl, biphenyl, furanyl, pyrrolyl, 1,2-diazolyl, imidazolyl, 1H,1,2,3-triazolyl, 1H-1,2,3,4-tetrazolyl, thiazolyl, oxazolyl, 1,3,4-thiadiazolyl, pyridinyl, pyrimidyl, 1,2-diazinyl, 1,4-diazinyl, 1,3,5-trizinyl, dibenzofuranyl, acridinyl, 2,1,3-benzothiadiazole, isoquinolinyl, quinolinyl, benzofuranyl, isobenzofuranyl, 1,3-benzodiazinyl, phenazinyl, phenoxazinyl, phenothiazinyl, pyran, chromenyl, xanthenyl, indolizinyl, isoindolyl, indolyl, purinyl, phthalazinyl, naphthyridinyl, quinoxalinyl, quinazolinyl, cinnolinyl, ptericinyl, carbazolyl, β-carbolinyl, phenanthridinyl, acridinyl, perimidinyl, phenanthrolinyl, isothiazoly, furazanyl, indolinyl, isoindolinyl, quinuclidinyl, and biotinyl.

Examples of aromatic moieties include, but are not limited to, phenyl naphthyl, 1-, 2-, or 3-biphenyl, indenyl, acenaphthylenyl, anthracenyl, phenanthrenyl, phenalenyl, triphenylenyl pyrenyl, and diphenylmethylenyl.

Examples of aliphatic moieties include, but are not limited to, straight-chain, branched and cyclic hydrocarbons; $C_{2-10}$ alkanes; $C_{3-10}$ alkenes containing 1 to 3 unsaturations; $C_{3-10}$ alkynes containing 1 to 3 unsaturations; branched $C_{3-10}$ alkanes, alkenes and alkynes; polycyclic aliphatic hydrocarbons and steroid-like ring systems that include $C_{3-8}$ cycloalkyl, adamantyl, camphoryl, and cholesteryl.

Moreover, the polyamine reactants used in reactions similar to that exemplified in FIG. 1A may be derivatized at one or more internal nitrogen and/or carbon positions along the linear backbone by a low molecular weight chemical moiety. Examples of such moieties are found in the following list:

| | | | |
|---|---|---|---|
| halogen | cyclohexyl | ethoxyl | propyl ester |
| methyl | cycloheptyl | propoxyl | isopropyl ester |
| ethyl | cyclooctyl | thio | cyano |
| propyl | cyclononyl | methylthio | isocyanato |
| isopropyl | cyclodecyl | ethylthio | trifluoromethyl |
| butyl | hexyl | propylthio | trichloromethyl |
| isobutyl | 2-hexyl | butylthio | tribromomethyl |
| tert-butyl | 3-hexyl | isopropylthio | azido |
| pentyl | allyl | nitro | Acetoxy |
| 2-pentyl | vinyl | amino | Carboxamide |
| 3-pentyl | acetylenic | acetamide | N-methylcarbox-amide |
| neopentyl | propargylic | formamide | N,N-dimethyl-carboxamide |
| cyclopentyl | homopropargylic | carboxylic | N-ethylcarboxamide |
| cyclopropyl | hydroxyl | methyl ester | N,N-diethylcarbox-amide |
| cyclobutyl | methoxyl | ethyl ester | |

Mono and multi-substituted forms of the moieties are also encompassed by the invention.

Preferred Polyamine Analogues and Derivatives

Figure 2:
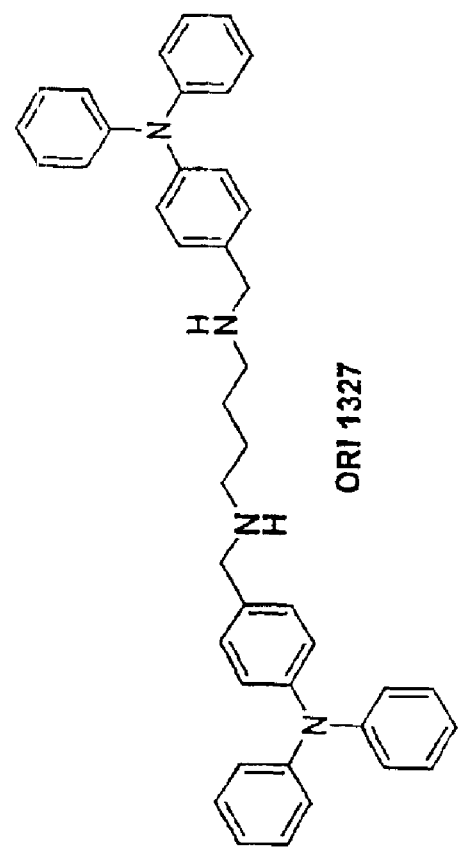
FIG. 2 shows the structures of polyamine analogues Ori 1313 and Ori 1327.
Figure 2:
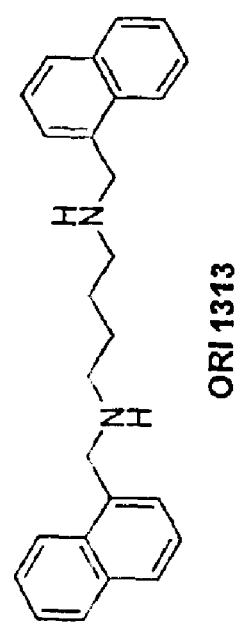

A preferred embodiment is a highly cytotoxic analogue with pharmaceutical utility as an anti-cancer chemotherapeutic. Preferred analogues with such activity include compounds 1313 and 1327 which have the structures shown in FIG. 2. These analogues are more potent than $N^1,N^4$-dibenzylputrescine, are cytotoxic to tumor cells at low micromolar concentrations, appear to induce apoptosis, and demonstrate efficacy in as little as one hour of treatment. Moreover, the analogues appear to induce apoptosis in tumor cell lines and are unexpectedly able to inhibit growth of tumor cell lines that express the multi-drug resistance. Furthermore, these analogues are also of particular specificity and efficacy for inhibiting cell growth and proliferation in melanoma cells.

Figure 3:
FIG. 3 is a table containing preferred polyamine analogues of the invention where the general structure of the analogues is shown at the top of the table. Included are analogues (or "Ori") 1313 and 1327. All structures shown are derived from putrescine (1,4-diaminobutane) unless otherwise noted.

Additional preferred compounds of the invention are putrescine analogues having the indicated R Groups as shown in FIG. 3 with the exception of analogues "1191" and "1192". The analogues listed by number in FIG. 3 are derivatives of putrescine whereby each indicated R Group is present on both terminal nitrogen atom positions. The indicated $IC_{50}$ values are for the human breast tumor cell line MDA-MB-231 ("MDA") and the human PC-3 prostate tumor cell line.

Further analogues of the invention include analogues of 1,3-diaminopropane, spermine, spermidine, and other polyamines derivatized with the R Groups of FIG. 3. For all linear polyamine analogues, including putrescine analogues, of the invention containing such R Groups, the derivatization need not be at both ends of the polyamine backbone, but may instead be at only one end.

Figure 4:
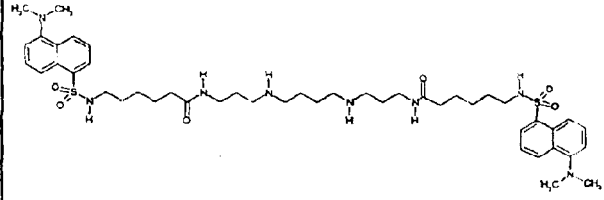
FIG. 4 is a table containing additional polyamine analogues of the invention.
Figure 4:
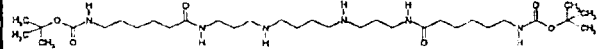
Figure 4:
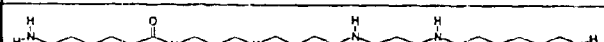
Figure 4:
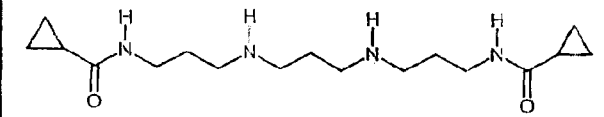
Figure 4:
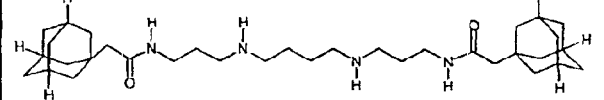
Figure 4:
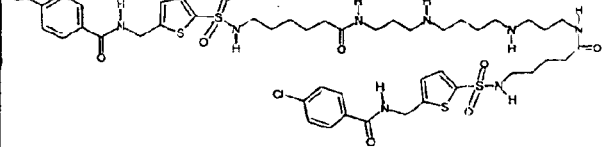
Figure 4:
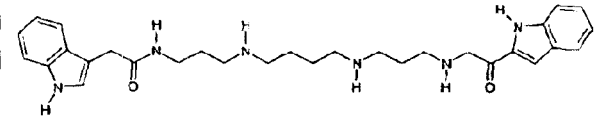
Figure 4:
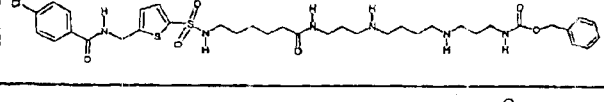
Figure 4:
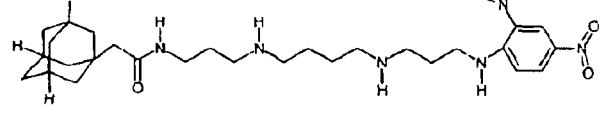
Figure 4:
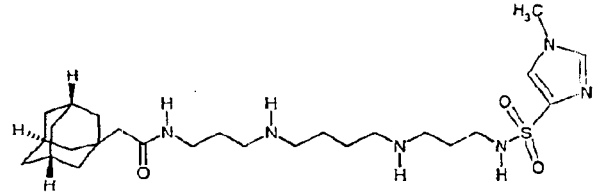

Additional analogues of the invention are shown in FIG. 4. It is readily apparent that the analogues are all of the formula $R_1$—X—$R_2$ as presented above. Thus each "$R_1$" and "$R_2$" group of FIG. 4 may be independently considered a moiety for the derivatization of any polyamine, including, but not limited to, 1,3-diaminopropane, putrescine, spermidine, and spermine.

Figure 11:
FIG. 11 is a table containing polyamine analogues, including halogenated analogues, of the invention.
Figure 11:
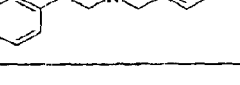
Figure 11:
Figure 11:
Figure 11:
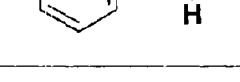
Figure 11:
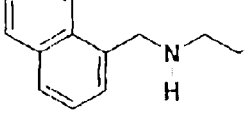
Figure 11:
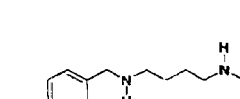
Figure 11:
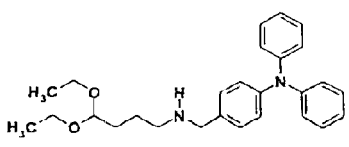
Figure 11:
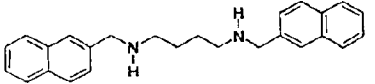
Figure 11:
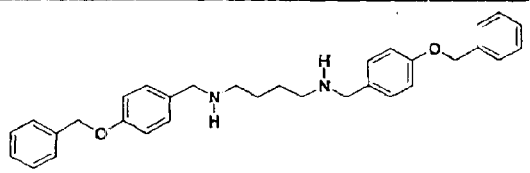
Figure 11:
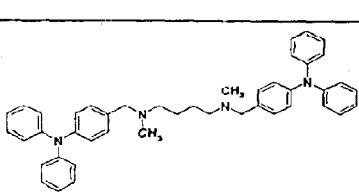
Figure 11:
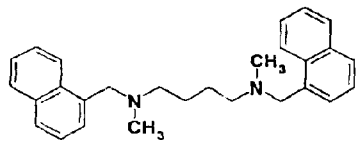
Figure 11:
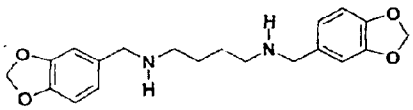
Figure 11:
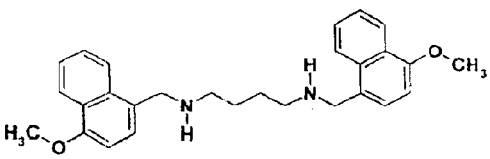
Figure 11:
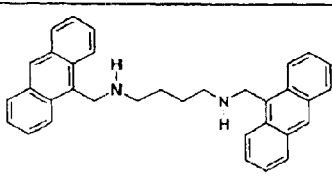
Figure 11:
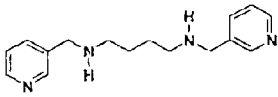
Figure 11:
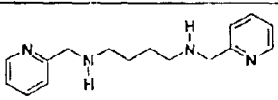
Figure 11:
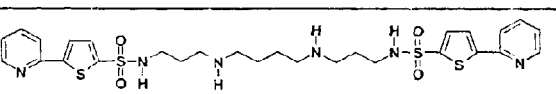
Figure 11:
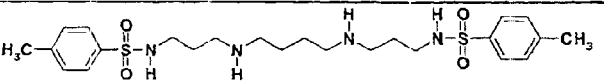
Figure 11:
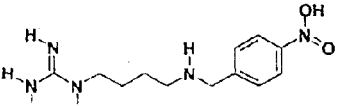
Figure 11:
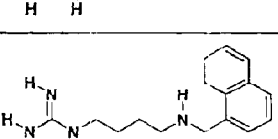
Figure 11:
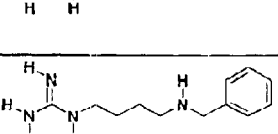
Figure 11:
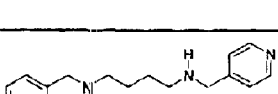
Figure 11:
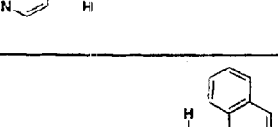
Figure 11:
Figure 12:
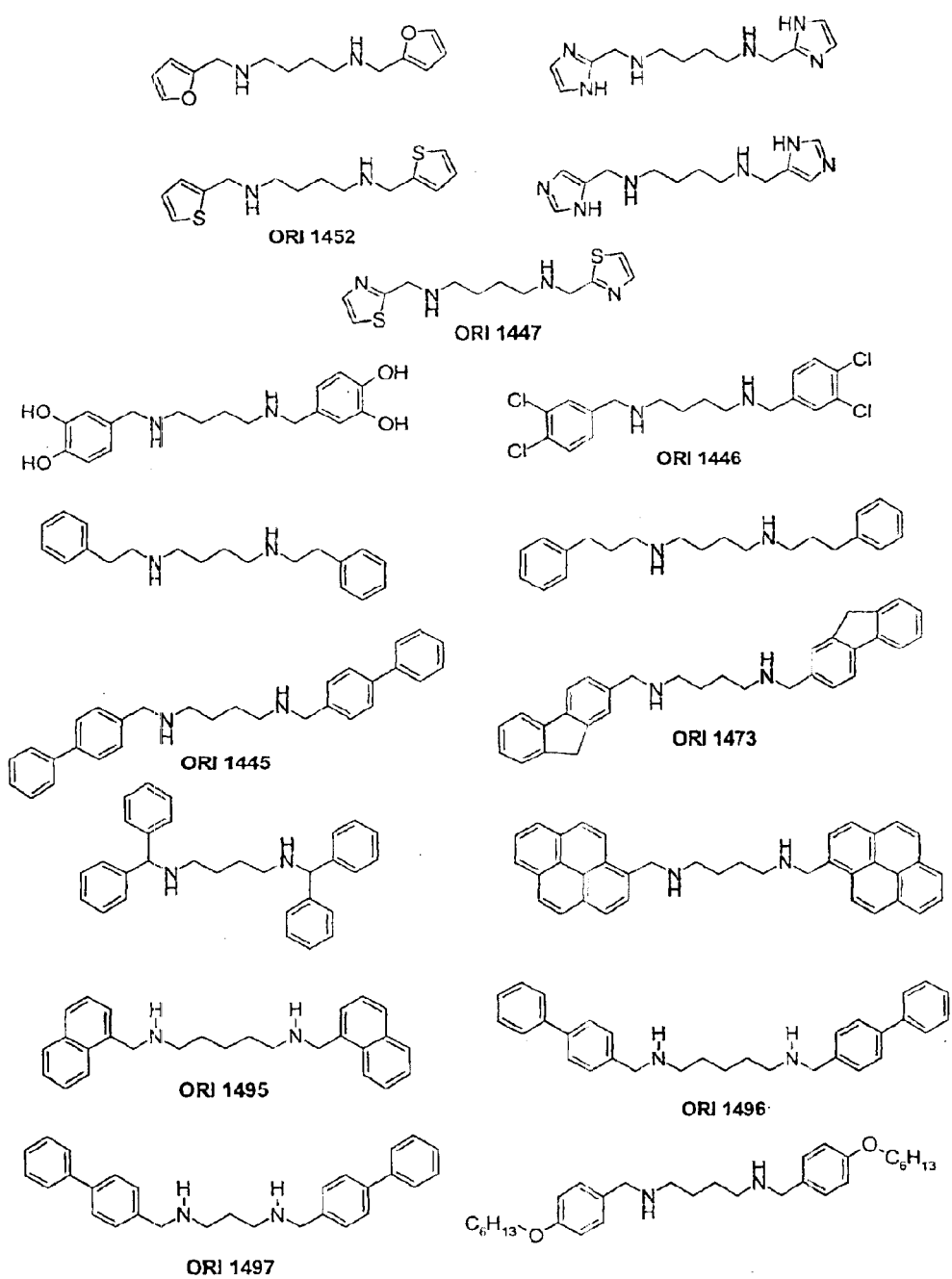
FIG. 12 shows additional symmetrical polyamine analogues of the invention, including halogenated analogues.

Other preferred compounds of the invention are shown in FIGS. 11 and 12. Of these, it is relevant to note that compounds 1441 and 1436 do not contain a linear polyamine as the core. Also, compound 1429 contains further substituents on internal carbon atoms of the polyamine. Compounds 1368, 1367, 1366, 1365, 1364, and 1363 comprise —$(CH_2)_3$—NH— as the core. They may also be viewed as asymmetrical polyamine analogues. In particular, compounds 1368 and 1367 may also be used as probes into the mechanism of action of cytotoxic polyamine analogue compounds. Other asymmetric polyamine analogues include compounds 1318, 1317, 1316, 1310, 1303, 1302, and 1301.

Preferred analogue compounds of the invention include derivatives of the compounds presented in FIGS. 3, 4, 11 and 12 as well as those with pharmaceutical utility as an anti-cancer, anti-viral, anti-microbial, anti-bacterial, anti-parasitic or anti-fungal chemotherapeutic based upon their cytotoxic properties.

The further derivatization or optimization of compounds having a desirable activity may be achieved by structural and functional comparisons with other polyamine analogues and derivatives of the invention to incorporate particular structural elements of other analogues into the compound being optimized. The structural elements will be selected based on the expectation of improving functionalities such as, but not limited to, cytotoxicity, metabolic stability, specificity, handling and administration, binding affinity, non-incorporation into cellular polyamine pools, and decreases in side effects.

The resultant compounds modified by the introduction of such structural elements may be of any structure, including those within the limits of the polyamine analogues and derivative structures defined herein. Stated differently, the resultant compounds may have one or more additional atoms or functional groups and/or removal of one or more atoms or functional groups after optimization, resulting in a compound either within or beyond the limits of the polyamine analogues and derivative structures defined herein.

Multiple iterations of optimizing compounds with preferred activity may be conducted to further improve the polyamine analogue.

Analytical and Diagnostic Uses

The polyamine analogues and derivatives of the invention may also be used as reporter molecules and probes to assay their localization with cellular factors which may be other pharmacological targets. Such factors include membranes, soluble and insoluble proteins, and nucleic acids.

Pharmaceutical and Therapeutic Compositions and Applications

The polyamine analogues and derivatives of the invention, as well as the pharmaceutically acceptable salts thereof, may be formulated into pharmaceutical compositions. Pharmaceutically acceptable acid salts of the compounds of the invention which contain basic groups are formed where appropriate with strong or moderately strong, non-toxic, organic or inorganic acids in the presence of the basic amine by methods known in the art. Exemplary of the acid salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. Additional illustrative acids which form suitable salts include hydrochloric, hydrobromic, sulfuric, and phosphoric acids; acetic, glycolic, lactic, pyruvic, malonic, succinic, glutaric, .alpha.-ketoglutaric, .alpha.-ketocaproic, .alpha.-ketoisocaproic, .alpha.-ketoisovaleric, fumaric, malic, tartaric, citric, ascorbic, maleic, hydroxymaleic, benzoic, hydroxybenzoic, phenylacetic, cinnimic, salicylic, and 2-phenoxybenzoic acids; and sulfonic acids such as methane sulfonic acid and 2-hydroxyethane sulfonic acid. Acid metal salts such as sodium monohydrogen orthophosphate and potassium hydrogen sulfate are also encompassed. As stated above, the compounds of the invention possess cytotoxic properties that are exploited in the treatment of any of a number of diseases or conditions, most notably cancer. A composition of this invention may be active per se, or may act as a "pro-drug" that is converted in vivo to active form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed. Pharmaceutical compositions designed for timed release may also be formulated.

Optionally, the compositions contain anti-oxidants, surfactants and/or glycerides. Examples of anti-oxidants include, but not limited to, BHT, vitamin E and/or C. Examples of glycerides include, but are not limited to, one or more selected from acetylated or unsubstituted monoglycerides; medium chain triglycerides, such as those found in oils; and caprylocaproyl macrogol-8 glycerides.

Preferably, the compounds of the invention are administered systemically, e.g., by injection or oral administration. When used, injection may be by any known route, preferably intravenous, subcutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, liquid containing capsule, sterile injectable liquid (e.g., a solution), such as an ampule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral or parenteral administration. Other preparations for topical, transdermal, intravaginal, intranasal, intrabronchial, intracranial, intraocular, intraaural and rectal administration may also be prepared. The pharmaceutical compositions may also contain minor amounts of nontoxic auxiliary substances such as wetting or emulsifying agents, pH buffering agents and so forth.

Although the preferred routes of administration are systemic, the pharmaceutical composition may be administered topically or transdermally, e.g., as an ointment, cream or gel; orally; rectally; e.g., as a suppository, parenterally, by injection or continuously by infusion; intravaginally; intranasally; intrabronchially; intracranially; intraaurally; or intraocularly.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams; gels; as well as petroleum jelly and the like.

Also suitable for topical application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the preferred topical applications, especially for humans, it is preferred to administer an effective amount of the compound to a target area, e.g., skin surface, mucous membrane, eyes, etc. This amount will generally range from about 0.001 mg to about 1 g per application, depending upon the area to be treated, the severity of the symptoms, and the nature of the topical vehicle employed.

The compositions of the invention be given in combination with one or more additional compounds that are used to treat the disease or condition. For treating cancer, the polyamine analogues and derivatives may be given in combination with anti-tumor agents, such as mitotic inhibitors, e.g., vinblastine; alkylating agents, e.g., cyclophosphamide; folate inhibitors, e.g., methotrexate, pritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase; topoisomerase inhibitors, e.g., etoposide; or biological response modifiers, e.g., interferon. In fact, pharmaceutical compositions comprising any known cancer therapeutic in combination with the polyamine analogues and derivatives disclosed herein are within the scope of this invention. The present compounds may also be administered in combination with a polyamine synthesis inhibitor such as DFMO.

The pharmaceutical compositions of the invention may also comprise one or more other medicaments such as anti-infectives including antibacterial, anti-fungal, anti-parasitic, anti-viral, and anti-coccidial agents.

Typical single dosages of the compounds of this invention are between about 1 ng and about 1 g/kg body weight. The dose is preferably between about 0.01 mg and about 500 mg/kg body wt. and, most preferably, between about 0.1 mg and about 100 mg/kg body wt. For topical administration, dosages in the range of about 0.01–20% concentration of the compound, preferably 1–5%, are suggested. A total daily dosage in the range of about 1–200 mg is preferred for oral administration. The foregoing ranges are, however, suggestive, as the number of variables in regard to an individual treatment regime is large, and considerable excursions from these recommended values are expected and may be routinely made by those skilled in the art.

Effective amounts or doses of the compound for treating a disease or condition can be determined using recognized in vitro systems or in vivo animal models for the particular disease or condition. In the case of cancer, many art-recognized models are known and are representative of a broad spectrum of human tumors. The compounds may be tested for inhibition of tumor cell growth in culture using standard assays with any of a multitude of tumor cell lines of human or nonhuman animal origin. Many of these approaches, including animal models, are described in detail in Geran, R. I. et al., "Protocols for Screening Chemical Agents and Natural Products Against Animal Tumors and Other Biological Systems (Third Edition)", *Canc. Chemother. Reports*, Part 3, 3:1–112.

Having now generally described the invention, the same will be more readily understood through reference to the following examples which are provided by way of illustration, and are not intended to be limiting of the present invention, unless specified.

EXAMPLE I

Cytotoxicity of Putrescine Analogs

Figure 5A:
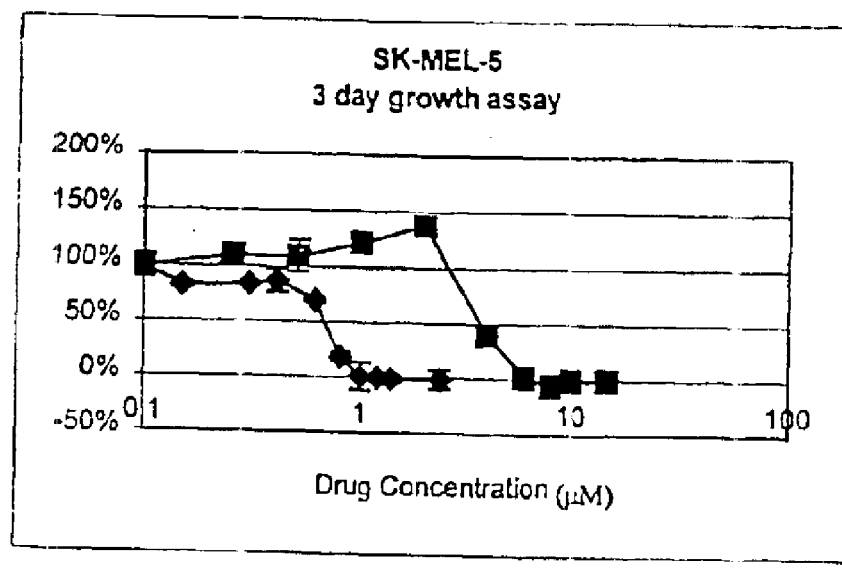
FIGS. 5A and 5B show cytotoxicity of ORI 1313 (-■-) and ORI 1327 (-♦-) against tumor cell lines (see Example 1 herein).
Figure 5B:
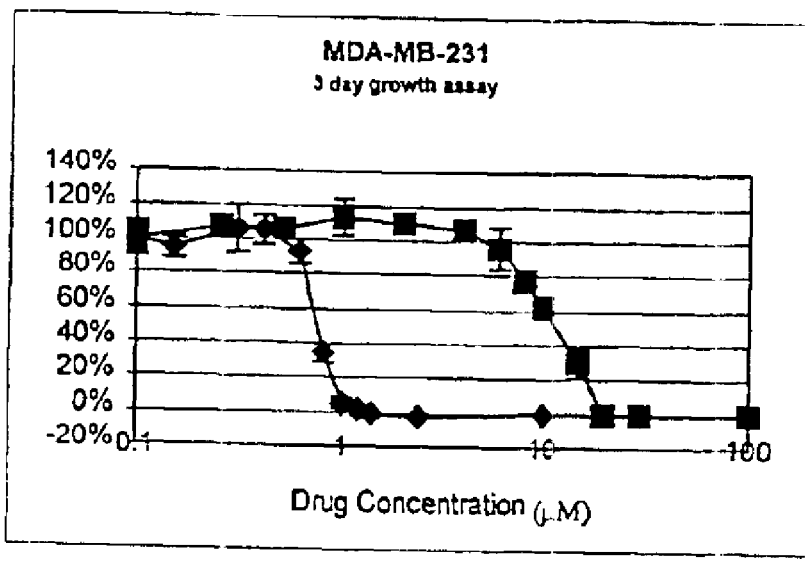

ORI 1313 and ORI 1327 displayed significant cytotoxic activity against SK-MEL-5 and MDA cell lines (see FIGS. 5A and 5B, ORI 1327, -◆-; ORI 1313, -■-). Briefly, cells were plated at 1500 (SK-MEL-5) or 5000 (MDA) cells/well in a 96-well plate and allowed to adhere for 1 day. The indicated analogues were added and the cells were incubated for 3 days, when cell growth was evaluated by MTS assay (Promega). Vertical axis represents cell number as a % of no drug treatment controls. Additionally, significant activity was seen against PC-3 cells (see FIGS. 4 and 11).

These two agents represent significant improvements in potency over $N^1, N^4$-dibenzylputrescine. $IC_{50}$ values against SK-MEL-5 cells were determined to be 4.1 μM and 0.71 μM for ORI 1313 and ORI 1327, respectively. The data shows ORI 1313 and ORI 1327 to have $IC_{50}$ values of 12 μM and 0.65 μM against MDA breast carcinoma cells, respectively. $N^1, N^4$-dibenzylputrescine showed an $IC_{50}$ of 192 μM when tested against the MDA cells. Thus ORI 1313 and ORI 1327 showed a 16-fold or 295-fold increase, respectively, over $N^1, N^4$-dibenzylputrescine in potency of cytotoxic activity against MDA cells.

$N^1, N^3$-dibenzyl analog of 1,3-diaminopropane has also been tested and determined to have an $IC_{50}$ value of 28.8 μM against MDA cells.

EXAMPLE II

Time Course of Polyamine Analogue Cytotoxicity in Tumor Cells

Figure 6A:
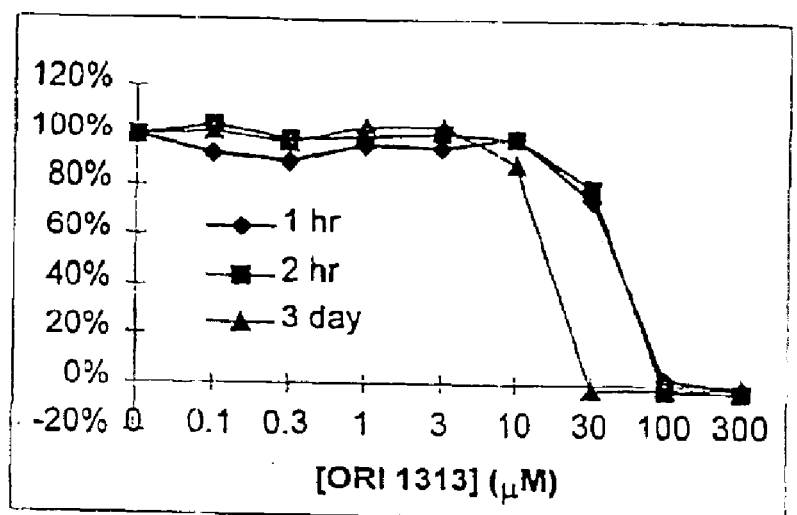
FIGS. 6A and 6B show time courses of ORI 1313 and OR 1327 cytotoxicity (see Example II herein).
Figure 6B:
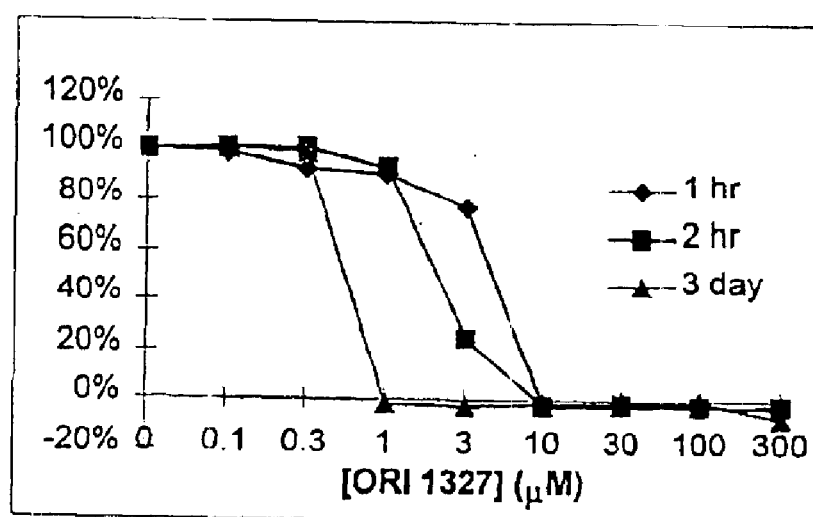

Even after only one hour of treatment, polyamine analogs displayed significant cytotoxicity in MDA cells (see FIGS. 6A and 6B). Briefly, MDA-MB-231 cells were plated at 5000 cells/well in a 96-well plate and allowed to adhere for 1 day. The indicated analogues were added and the cells were incubated for the various times shown. The cells were then washed and fresh analogue-free media was added. After a total of 3-days, cell growth was evaluated by MTS assay (Promega). Vertical axis represents cell number as a % of no drug treatment controls These findings suggest that the polyamine analogues can induce cytotoxicity without need for prolonged depletion of polyamines and that removal of the drug from the medium does not enable the cells to recover or regrow. This observation may have significant implications in the clinical use of these agents. Given a sufficiently high selectivity for cancer versus normal cells, contact with a threshold concentration of the analogue for a relatively short period will induce tumor cell death without need for maintenance of analogue concentration. Thus high, sustained levels of analogue or prolonged treatments may not be required for effective anti-tumor therapy with these compounds.

EXAMPLE III

Cytotoxic Polyamine Analogues Induce Apoptosis

Figures 7A, 7B, 7C:
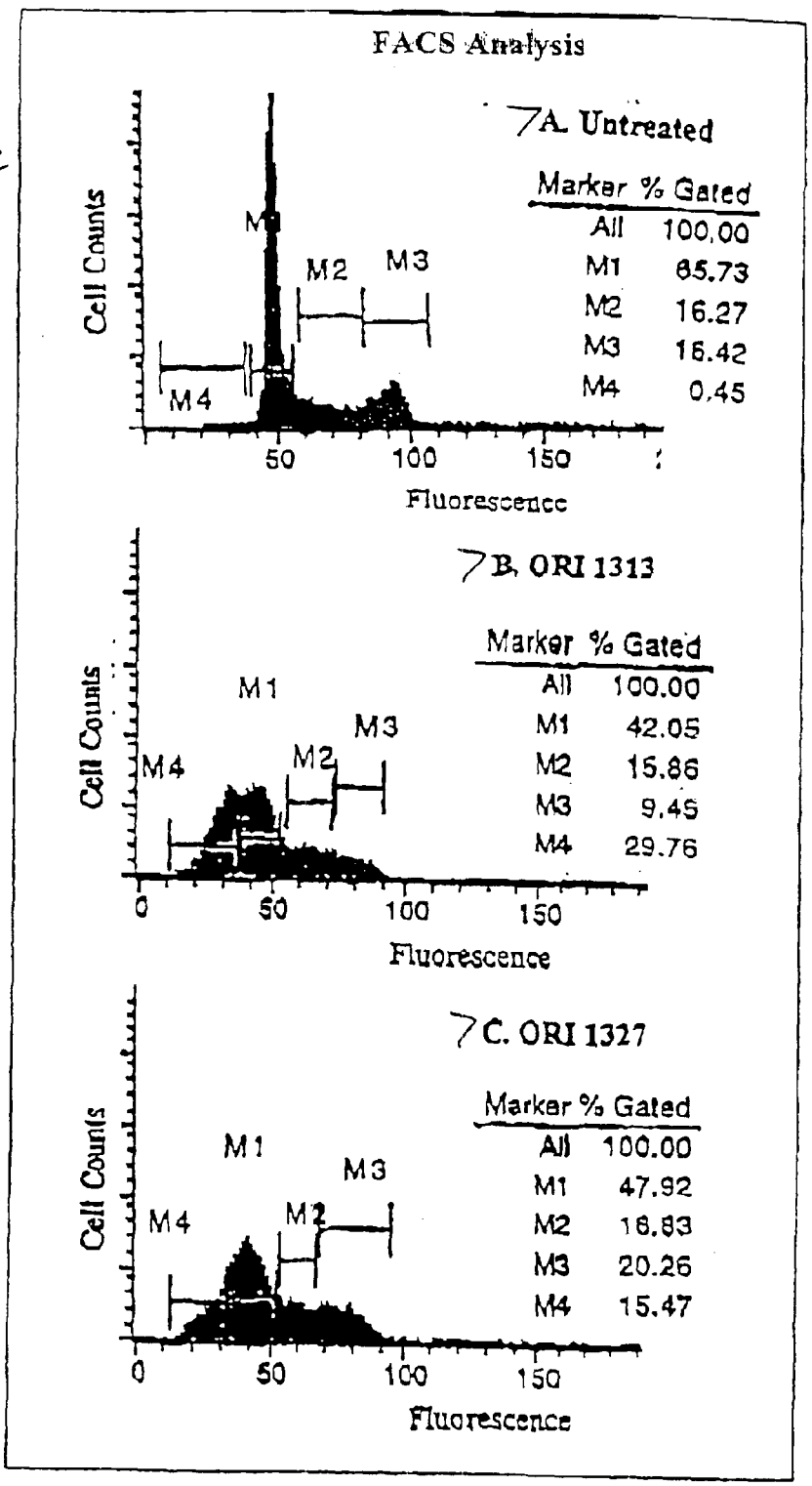
FIGS. 7A–7C show induction of apoptosis by polyamine analogues OR 1313 and ORI 1327.

Cell cycle analysis was performed using fluorescent activated cell sorter (FACS) analysis on polyamine analogue treated MDA cells (see FIGS. 7A–7C). Briefly, MDA-MB-231 cells were grown in the presence of ORI 1313 or ORI 1327 for various times then fixed with ethanol and stained with propidium iodide. Cells were analyzed by FACS, with the areas on the histograms designating DNA content and cell cycle stage: M1, G1; M2, S; M3, G2/M; M4, <2N (apoptotic cells). FIG. 7A shows the results with untreated cells; 7B shows the results with 32 $\mu$M ORI 1313 treatment for 48 hours; and 7C shows the results with 3 $\mu$M ORI 1327 treatment for 11 hours.

This analysis showed a high apoptotic fraction after ORI 1313 treatment (32 $\mu$M, 11 hr treatment gave 21%, 24 hr treatment gave 49% and 48 hr treatment gave 30% <2N DNA content) and showed moderate apoptotic cells after ORI 1327 treatment (3 $\mu$M, 11 hr treatment gave 15% <2N DNA content). These data show that the analogues potently induce the cell death apparatus of the tumor cells

EXAMPLE IV

Cytotoxic Polyamine Analogues are Cytotoxic for MDR Tumor Cells

Figure 8A:
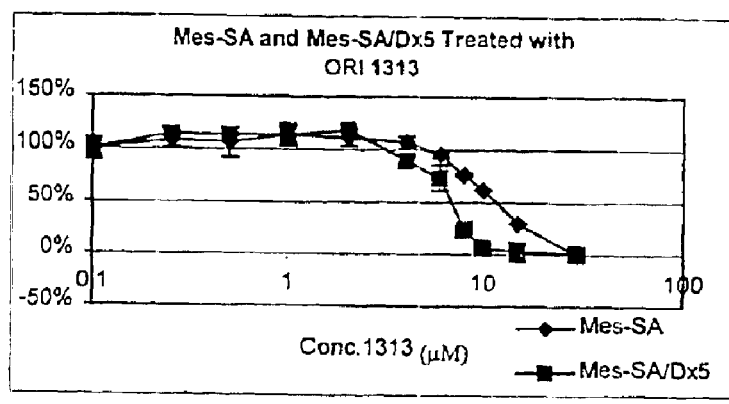
FIGS. 8A and 8B show cytotoxicity for tumor cells expressing MDR-1 by polyamine analogues ORI 1313 and ORI 1327.
Figure 8B:
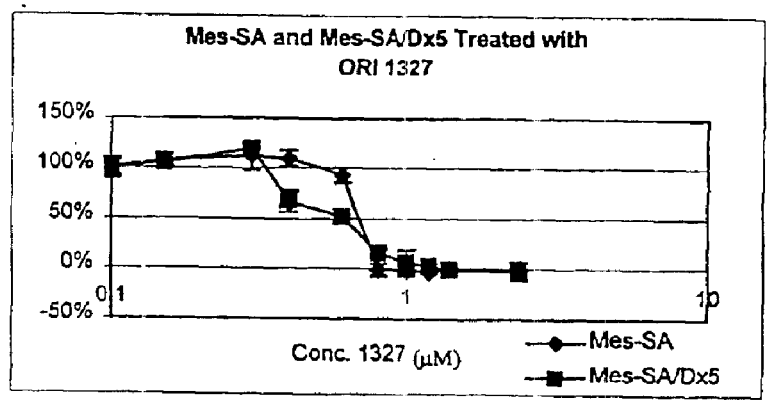

An unexpected observation made during the cellular characterization of ORI 1313 and ORI 1327 was their growth inhibitory activity against the multi-drug resistant (MDR) uterine sarcoma cell line, MES-SA/Dx5 (see FIGS. 8A and 8B). Briefly, cells were plated at 1000 cells/well in a 96-well plate and allowed to adhere for 1 day. The indicated analogue was added and the cells were incubated for 3 days when cell growth was evaluated by MTS assay (Promega). Vertical axis represents cell number as a % of no drug treatment controls The MES-SA/Dx5 cell line was developed by selection on doxorubicin and over-expresses the mRNA of the multi-drug resistance gene (MDR-1). The cells are thus much less sensitive to drugs exported via P-glycoprotein (P-gp). See Harker, W. G. et al. Multi-drug (pleiotropic) resistance in doxorubicin-selected variants of the human sarcoma cell line MES-SA. *Cancer Research,* 1985, 45, 4091–4096. Similar growth inhibition curves against the parent and resistant cell lines (FIGS. 8A and 8B) strongly suggest that ORI 1313 and ORI 1327 are not substrates for the P-gp multi-drug exporter. This will be particularly advantageous in situations involving target cells expressing MDR-1.

EXAMPLE V

Cytotoxic Polyamine Analogues do not Alter Cellular Polyamine Levels

Figure 9:
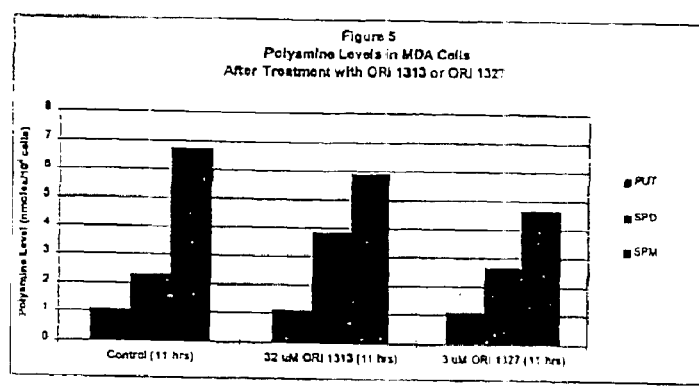
FIG. 9 shows that the polyamine analogues ORI 1313 and ORI 1327 do not alter cellular polyamine levels.

To determine the effects of treatment with polyamine analogues on cellular polyamine levels, intracellular polyamine levels were measured by high performance liquid chromatography (HPLC) after 11 hr treatment with ORI 1313 (32 $\mu$M) or ORI 1327 (3 $\mu$M). These results showed no significant effects on the polyamine levels after drug treatment (see FIG. 9). This observation is consistent with the previous observations in the field. Moreover, measurement of SSAT activity in treated cells showed no induction of this enzyme (data not shown).

A follow-up experiment showed that co-treatment with a 50-fold excess concentration of putrescine did not block the cytotoxic effects of ORI 1313 or ORI 1327 treatment. Co-treatment with 1 mM DFMO did not alter the results observed with ORI 1313 or ORI 1327 Co-treatment with a potent polyamine transport inhibitor, ORI 1202 (with $K_i$ values of 32±15 nM and 29±9 nM versus $^3$H-spermidine and $^3$H-putrescine uptake, respectively, in MDA cells and which effectively depletes cellular putrescine and spermidine when used in combination with a polyamine biosynthesis inhibitor such as DFMO), also did not alter the observed inhibition of cell growth by ORI 1313 or ORI 1327.

The cellular uptake mechanism for these polyamine analogues was further explored by their inhibition of $^3$H-putrescine uptake. Putrescine was previously shown to have a $K_m$ of 12.4 $\mu$M for uptake into MDA cells. ORI 1313 showed a $K_{iapp}$ of 28.3 $\mu$M versus putrescine uptake into MDA cells and 24.1 $\mu$M into PC-3 cells. ORI 1327 showed a $K_{iapp}$ of 14.3 $\mu$M versus putrescine uptake into PC-3 cells. These results suggest that the polyamine transporter is a possible mode of cellular uptake for these analogs. Nevertheless, since co-treatment with 50-fold excess putrescine, co-treatment with the polyamine biosynthesis inhibitor DFMO (previously shown to stimulate the uptake of polyamine analogs via the polyamine transporter) and co-treatment with the potent polyamine transport inhibitor ORI 1202 all failed to modify the effects of the analogues, it appears that the analogues may enter cells by alternative uptake mechanisms.

Since it has been established that tumor cells have a greater requirement for polyamines and this higher requirement is met by the increased uptake and biosynthesis of polyamines (see Heston, W. D. W. et al. Differential effect of alpha-difluoromethylornithine on the in vivo uptake of C-14 labeled polyamines and methylglyoxal bis (guanylhydrazone) by a rat prostate-derived tumor. *Cancer Res.* 1984, 44, 1034–1040; Minchin, R. F. et al. Paraquat is not accumulated in B16 tumor cells by the polyamine transport-system. *Life Sci.,* 1989, 45, 63–69; McCormack, S. A. et al. Putrescine uptake and release by colon cancer cells. *Am. J. Physiol.* 1989, 256, G868–G877; and Dave, C. et al. Studies in the mechanism of cytotoxicity of methylglyoxal bis(guanylhydrazone) in cultured leukemia L1210 cells. *Adv. Polyamine Res.* 1978, 1, 153–171), the polyamine analogue nature of ORI 1313 and ORI 1327 might cause them to be selectively accumulated in tumor cells. Byers and coworkers showed that the uptake of a series of benzylated spermine analogs with anti-malarial properties was distinct from the polyamine transport system (see Byers, T. L. et al. Bis(benzyl)polyamine analogues are substrates for a mammalian cell transport system which is distinct from the polyamine-transport system. *Biochem. J.* 1990, 269, 35–40).

EXAMPLE VI

Involvement of Caspase-3 in Polyamine Analogue Cytotoxicity

Figure 10:
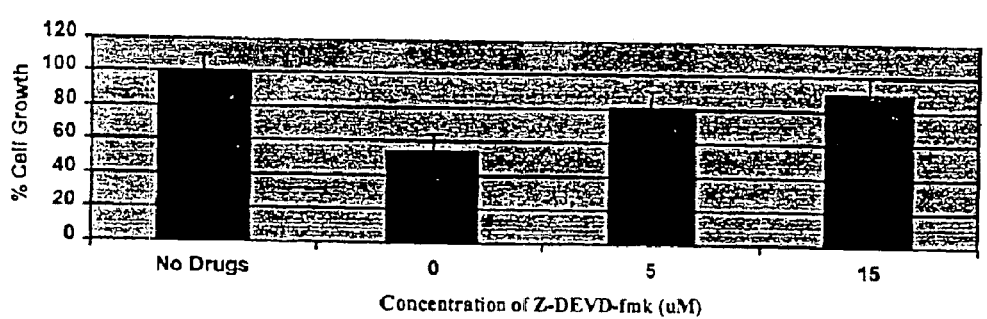
FIG. 10 shows that cytotoxicity of polyamine analogue ORI 1313 involves caspase-3 (see Example VI herein).

Involvement of the pro-apoptotic caspase-3 enzyme in the action of OR 1313 is shown by the experiment represented in FIG. 10. Briefly, PC-3 cells were plated at 1000 cells/well in a 96-well plate and allowed to adhere for 1 day. 10 $\mu$M of ORI 1313 and 0, 5, or 15 $\mu$M Z-DEVD-fmk, a caspase inhibitor, were added and the cells were incubated for 3 days. Cell growth was evaluated by MTS assay (Promega). Vertical axis represents cell number as a % of no drug treatment controls.

Treatment with 10 $\mu$M ORI 1313 alone caused a 46% inhibition of growth of PC-3 prostate cancer cells. When the cells were co-treated with 10 $\mu$M ORI 1313 and 5 or 15 $\mu$M of the caspase inhibitor Z-DEVD-fmk the growth inhibition decreased to 19% and 10%, respectively. This indicates that inhibition of a caspase enzyme reduced the cytotoxicity of ORI 1313, suggesting that such an enzyme plays a role in the cytotoxic mechanism of ORI 1313.

In a separate experiment, caspase-3 protease activity was measured in PC-3 cells treated with ORI 1313 (30 $\mu$M) and ORI 1327 (2 $\mu$M) for 14 hr. Doxorubicin (5 $\mu$M) was used as a positive control. The ApoAlert Caspase-3 Assay Kit from Clontech Laboratories was used to monitor the proteolytic activity. Untreated control cells were determined to have 10.2±0.3 units/2×10$^6$ cells of caspase-3 activity. Doxorubicin treated cells showed 13.5±0.2 units/2×10$^6$ cells of activity. ORI 1313 and ORI 1327 showed 12.7±1.2 and 11.6±0.8 units/2×10$^6$ cells of activity. These results confirmed the activation of caspase-3 activity in PC-3 cells after treatment with ORI 1313 or ORI 1327. Alterations in polyamine analogue concentration and treatment time may further increase caspase activity beyond that observed with doxorubicin.

Without being bound by theory, the polyamine analogues of the present invention may participate in an apoptosis mechanism by having an effect on mitochondria permeability transition and affecting the inner mitochondrial membrane where the release of cytochrome c is induced. This is based on comparisons with recent reports on the effects of polyamines on mitochondria permeability transition. If a polyamine analogue of the invention acts via such a mechanism, it would represent a unique mechanism of action compared to other polyamine cytotoxic agents. Experimental confirmation of this mechanism is available by 1) measuring cellular uptake and localization of these agents using HPLC analysis; 2) measuring the mitochondrial permeability transition on isolated mitochondria using light-scattering methods; 3) Western-blot analysis of the release of cytochrome c from isolated mitochondria and whole cells; and 4) exploring the sequence and timing of induction of the steps to apoptosis with these agents and compare to standard apoptosis-inducing agents. These experiments would be based upon well-established literature procedures and would not require undue experimentation.

EXAMPLE VII

Selectivity for Melanoma Cells by Polyamine Analogues 1313 and 1327

ORI 1313 and ORI 1327 were evaluated by the National Cancer Institute (NCI) with a 60-cell line screen. A surprising effectiveness was observed for ORI 1313 against 6 of 8 melanoma cell lines tested, which is consistent with previous observations with $N^1$, $N^4$-dibenzylputrescine in a melanoma xenograft animal model (see Frydman et al.) and suggests a dramatic selectivity at least for melanoma cell lines. Comparison of IC$_{50}$ values determined by the present inventors and NCI confirms these data: ORI 1313 in MDA cells, 12 vs. 2.3 $\mu$M, in PC-3 cells, 20 vs. 11.2 $\mu$M; ORI 1327 in MDA cells, 0.65 vs. 0.005 $\mu$M, in PC-3 cells, 0.65 vs. 0.81 $\mu$M.

EXAMPLE VIII

Solubility and In Vivo Toxicity of Pol Amine Analogues

The dihydrochloride salt of ORI 1313 is soluble in 5% DMSO (dimethyl sulfoxide) to at least 40 mM. ORI 1327 displays a more limited aqueous solubility. The maximum solubility of the lactate salt of ORI 1327 is 5 mM. The dihydrochloride salt is less soluble. Significant improvements in the solubility were made by the use of hydroxypropyl-$\beta$-cyclodextrin (45% w/v H$\beta$C in H$_2$O). A 40 mM solution of ORI 1327 was produced in this manner.

Mouse tolerance to drug treatment has been evaluated for ORI 1313 and ORI 1327. Acute toxicities following single intraperitoneal (i.p.) injections of ORI 1313 or ORI 1327 were evaluated in BALB/c mice. ORI 1313 was tolerated at 93 mg/kg. A dose of 186 mg/kg caused death in the animals (mice appeared lethargic and had ruffled fur before death). ORI 1327 was tolerated at 37 mg/kg, and a dose of 75 mg/kg caused death in the animals. Chronic toxicities were evaluated by giving i.p. injections once daily for 5 consecutive days. ORI 1313 and ORI 1327 were tolerated at 40 mg/kg and 7.5 mg/kg doses, respectively. Dosages of 80 and 30 mg/kg, respectively, proved lethal. These data, in comparison with the foregoing in vitro experiments, indicate that potentially efficacious dosages of these compounds are tolerated in mice. The approximate maximum tolerated dosages in a one i.p. injection a day for 5 days regimen are 40 mg/kg for ORI 1313 and 7.5 mg/kg for ORI 1327.

EXAMPLE IX

Analogue Cytotoxicity against Human Tumor Xenografts in Nude Mice

Figure 13:
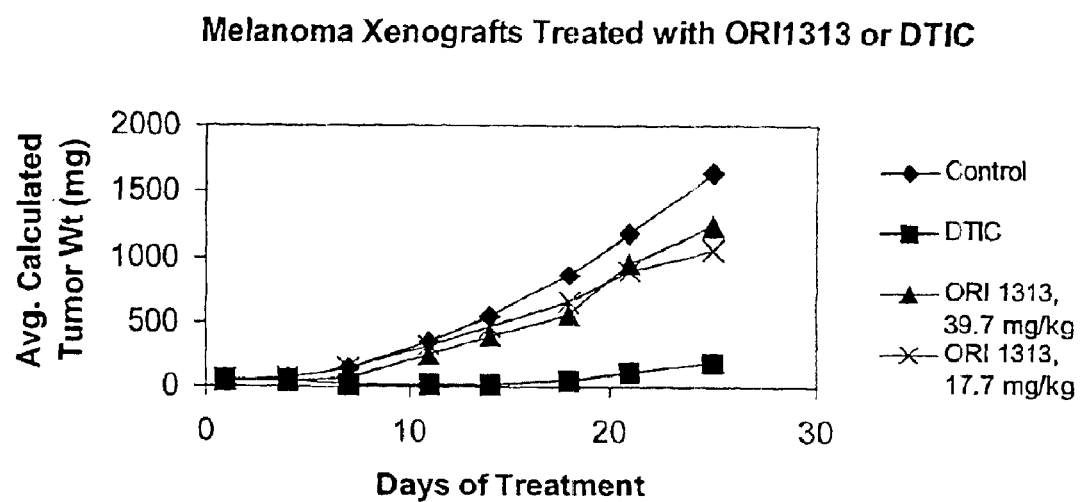
FIG. 13 is a graph illustrating inhibition of tumor growth in ORI 1313 treated A375 human melanoma xenografts in mice (see Example IX herein).

ORI was tested in a melanoma tumor xenograft tumor models in BALB/c nude mice. The A375 human melanoma cell line was chosen due to good activity by the analogue against this line in the NCI's 60-cell line test and the low IC$_{50}$ value determined against this cell line (ORI 1313, 4.1 $\mu$M). The xenograft efficacy study would be performed with two drug concentrations. There were four groups of 10 mice. Treatment groups received the maximum tolerated dose (MTD) or ½ MTD of each analogue. Compared to a negative control group treated with 5% dextrose, ORI 1313 inhibited A375 melanoma growth: 36% growth inhibition at 25 days and 6.2 day tumor growth delay (see FIG. 13). The drug was well tolerated up to 7 weeks. Some transient skin ulceration and weight loss was seen after 7 weeks of treatment. A positive control group treated with dacarbazine DTIC (dosage of 180 mg/kg i.p. once per day for 5 days) was used to validate this tumor model system.

Female BALB/c nu/nu athymic mice weighing 20 grams were the animal host for the human xenografts. The method of administration was i.p. injections with 9 mM or 4 mM ORI 1313 once daily for the duration of the study (end point when control tumors reached 2000 mg). The mode of delivery and dosing schedule may be further optimized by routine methods. DITC was administered by i.p. injection once daily for 5 days. Treatment started when the tumors reach 5 mm×5 mm size (50 mg). The mouse weight and tumor size were measured twice weekly. The tumor measurements by calipers were then converted to mg tumor volume by the formula $L^2 \times W/2$. Once the control tumors reached 2000 mg both the control and treatment group mice were weighed, sacrificed and the tumors removed. The actual weights of tumors were then used to calculate the percent growth inhibition by each analogue using the formula: % growth inhibition=(mean treated tumor weight/mean control tumor weight×100)−100.

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A polyamine analogue having the structure selected from the group consisting of:

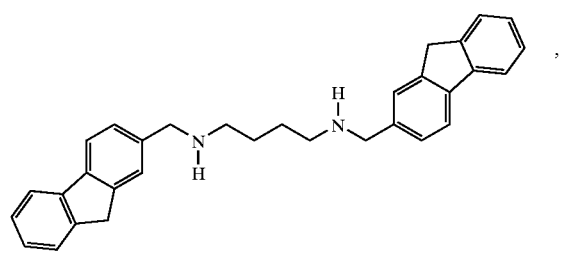

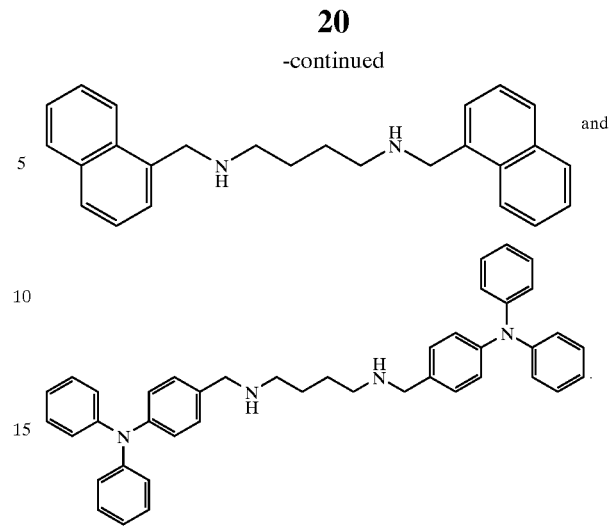

2. The analogue according to claim 1, wherein said structure is:

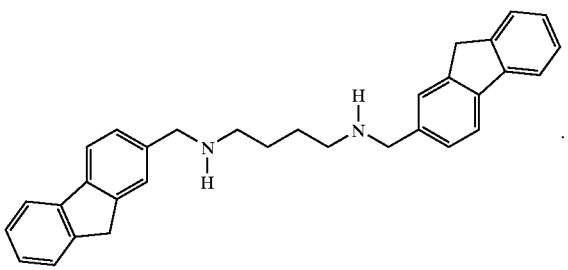

3. The analogue according to claim 1 wherein said structure is:

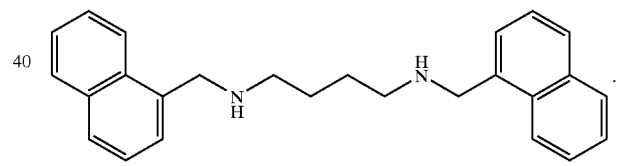

4. The analogue according to claim 1 wherein said structure is:

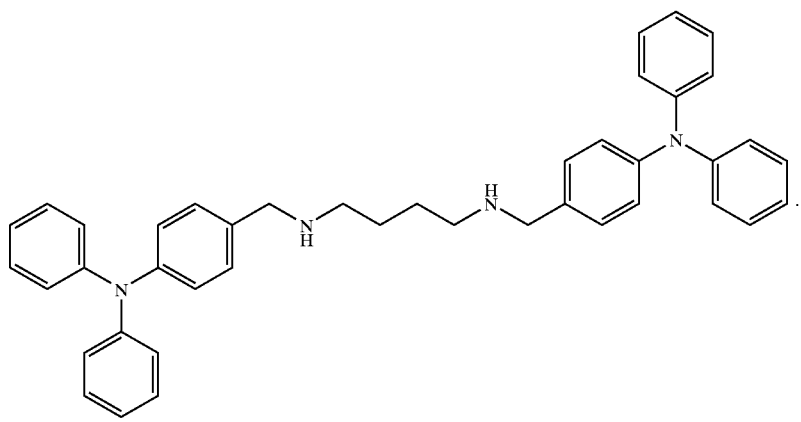

5. A pharmaceutical composition useful for treating a disease or condition in which the inhibition of cell growth or proliferation is desirable, comprising a polyamine analogue according to claim 1, and a pharmaceutically acceptable excipient.

6. The composition of claim 5 further comprising one or more additional agents known to be useful for treating said disease or condition.

7. A method for treating a disease or a condition in a subject associated with undesired cell growth or proliferation which comprises administering to said subject an effective amount of a polyamine analogue according to claim 1.

8. The method of claim 7 wherein said undesired cell growth or proliferation is associated with proliferation of cells of the immune system, cells of the vascular neointima, tumor cells or with undesired angiogenesis.

9. The method according to claim 7 wherein said disease or condition is cancer or post-angioplasty injury.

10. The composition according to claim 5 wherein said disease is osteoporosis.

11. The composition of claim 5 formulated for intravenous, subcutaneous, intramuscular, intracranial, intraperitoneal, topical, oral, transdermal, intravaginal, intranasal, intrabronchial, intraocular, intraaural or rectal administration.

12. The composition of claim 5 formulated as an ointment, cream, gel, solution, suspension, emulsion, powder, liniment, or salve.

13. The method of claim 7 wherein said disease is osteoporosis.

* * * * *